US008939919B2

(12) United States Patent
Barlow et al.

(10) Patent No.: US 8,939,919 B2
(45) Date of Patent: Jan. 27, 2015

(54) ENHANCED THERAPEUTIC STIMULUS SYSTEM AND METHODS OF USE

(75) Inventors: Steven M. Barlow, Lawrence, KS (US); David L. Stalling, Shawnee, IN (US); Kenneth Aron, Shawnee, KS (US)

(73) Assignees: Innara Health, Inc., Shawnee, KS (US); University of Kansas, Lawrence, KS (US)

( * ) Notice: Subject to any disclaimer, the term of this patent is extended or adjusted under 35 U.S.C. 154(b) by 121 days.

(21) Appl. No.: 13/457,059

(22) Filed: Apr. 26, 2012

(65) Prior Publication Data

US 2013/0289648 A1   Oct. 31, 2013

(51) Int. Cl.
| | |
|---|---|
| *A61B 5/103* | (2006.01) |
| *A61J 17/00* | (2006.01) |
| *A61B 5/03* | (2006.01) |
| *A61B 5/00* | (2006.01) |

(52) U.S. Cl.
CPC .............. *A61B 5/038* (2013.01); *A61B 5/6896* (2013.01)
USPC .......................................... 600/590; 434/258

(58) Field of Classification Search
USPC .................................. 607/42, 45, 2, 134, 48
See application file for complete search history.

(56) References Cited

U.S. PATENT DOCUMENTS

| | | | |
|---|---|---|---|
| 4,232,687 | A | 11/1980 | Anderson-Shanklin |
| 5,830,235 | A | 11/1998 | Standley |
| 6,033,367 | A | 3/2000 | Goldfield |
| 7,435,232 | B2 | 10/2008 | Liebschner |
| 7,917,201 | B2 | 3/2011 | Gozani et al. |
| 8,157,731 | B2 | 4/2012 | Teller et al. |
| 8,226,579 | B2 | 7/2012 | Barlow et al. |
| 8,251,926 | B2 | 8/2012 | Barlow et al. |
| 2004/0019382 | A1 | 1/2004 | Amirouche et al. |
| 2006/0074354 | A1 | 4/2006 | Barlow et al. |
| 2006/0079814 | A1 | 4/2006 | Barlow et al. |
| 2009/0156967 | A1 | 6/2009 | Cohen |
| 2009/0222214 | A1 | 9/2009 | Barlow et al. |

(Continued)

FOREIGN PATENT DOCUMENTS

| | | |
|---|---|---|
| CN | 101080195 B1 | 11/2012 |
| EP | 1786319 B1 | 10/2012 |

(Continued)

OTHER PUBLICATIONS

Barlow et al, "Synthetic orocutaneous stimulation entrains preterm infants with feeding difficulties to suck." J Perinatol, 2008, pp. 541-548, vol. 28, No. 8.

(Continued)

*Primary Examiner* — Carl H Layno
*Assistant Examiner* — Jon Eric C Morales
(74) *Attorney, Agent, or Firm* — Polsinelli PC

(57) ABSTRACT

The present invention relates to a therapeutic system and methods of using the therapeutic system. In particular, the present invention relates to systems having hardware, software, and appliance components for assessing and entraining a neuromuscular pattern or behavior in a patient. The methods include configuring the hardware and software systems to receive data from an orofacial stimulation appliance and to generate a precise therapeutic pulse profile that is actuated as a tactile stimulus. In one embodiment, the system and methods also include collecting data using the orofacial stimulation appliance and delivering the tactile stimulus via the orofacial stimulation appliance to entrain an organized neuromuscular pattern or behavior.

33 Claims, 27 Drawing Sheets

(56) References Cited

U.S. PATENT DOCUMENTS

2010/0075285 A1 3/2010 Stalling et al.
2011/0060252 A1 3/2011 Simonsen et al.
2012/0209148 A1* 8/2012 Barlow et al. .............. 600/590

FOREIGN PATENT DOCUMENTS

| GB | 1206014 A | 9/1970 |
|---|---|---|
| WO | 2006026623 A2 | 3/2006 |
| WO | 2006081376 A1 | 8/2006 |
| WO | 2008067607 A1 | 6/2008 |

OTHER PUBLICATIONS

Goldfield et al.; "Coordination of Sucking, Swallowing, and Breathing and Oxygen Saturation During Early Infant Breast-feeding and Bottle-feeding"; Pediatric Research; vol. 60;/ No. 4; pp. 450-455; Oct. 2006.

Poore et al., "Respiratory treatment history predicts suck pattern stability in preterm infants." J Neonatal Nurs, 2008, pp. 185-192, vol. 14, No. 6.

European Application Serial No. 09250464.6, Office Action mailed Mar. 22, 2012, 11 pgs.

Estep et al., "Non-Nutritive Suck Parameter in Preterm Infants with RDS." J Neonatal Nurs, 2008, pp. 28-34, vol. 14, No. 1.

Stumm et al., "Respiratory Distress Syndrome Degrades the Fine Structure of the Non-Nutritive Suck in Preterm Infants." J Neonatal Nurs, 2008, pp. 9-16, vol. 14, No. 1.

Vantipalli et al.; Somatosensory entrainment of suck in preterm infants: NTrainer CNL Technical Research Report; 2006; 3:1-23 entire document.

PCT/US2013/038405 International Search Report and Written Opinion mailed Jul. 11, 2013; (10 pages).

PCT/US2013/038410 International Search Report and Written Opinion mailed Jul. 15, 2013 (8 pages).

PCT/US13/38400 International Search Report and Written Opinion mailed Jul. 19, 2013 (15 pages).

* cited by examiner

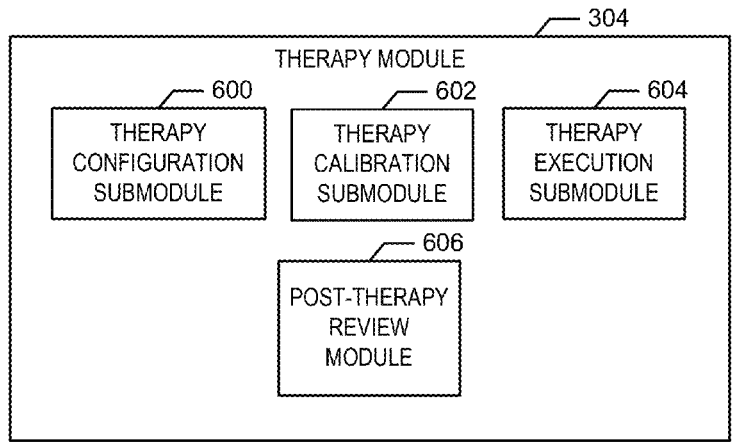
FIG. 6
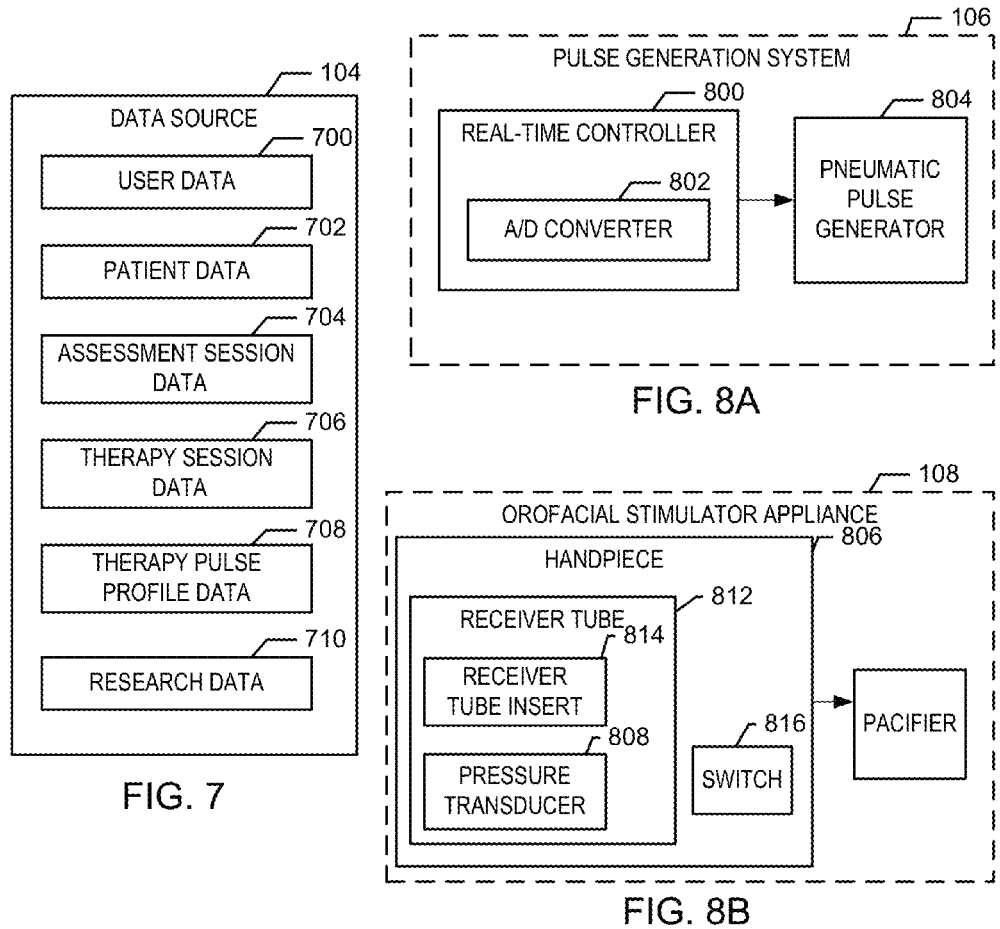
FIG. 7
FIG. 8A
FIG. 8B

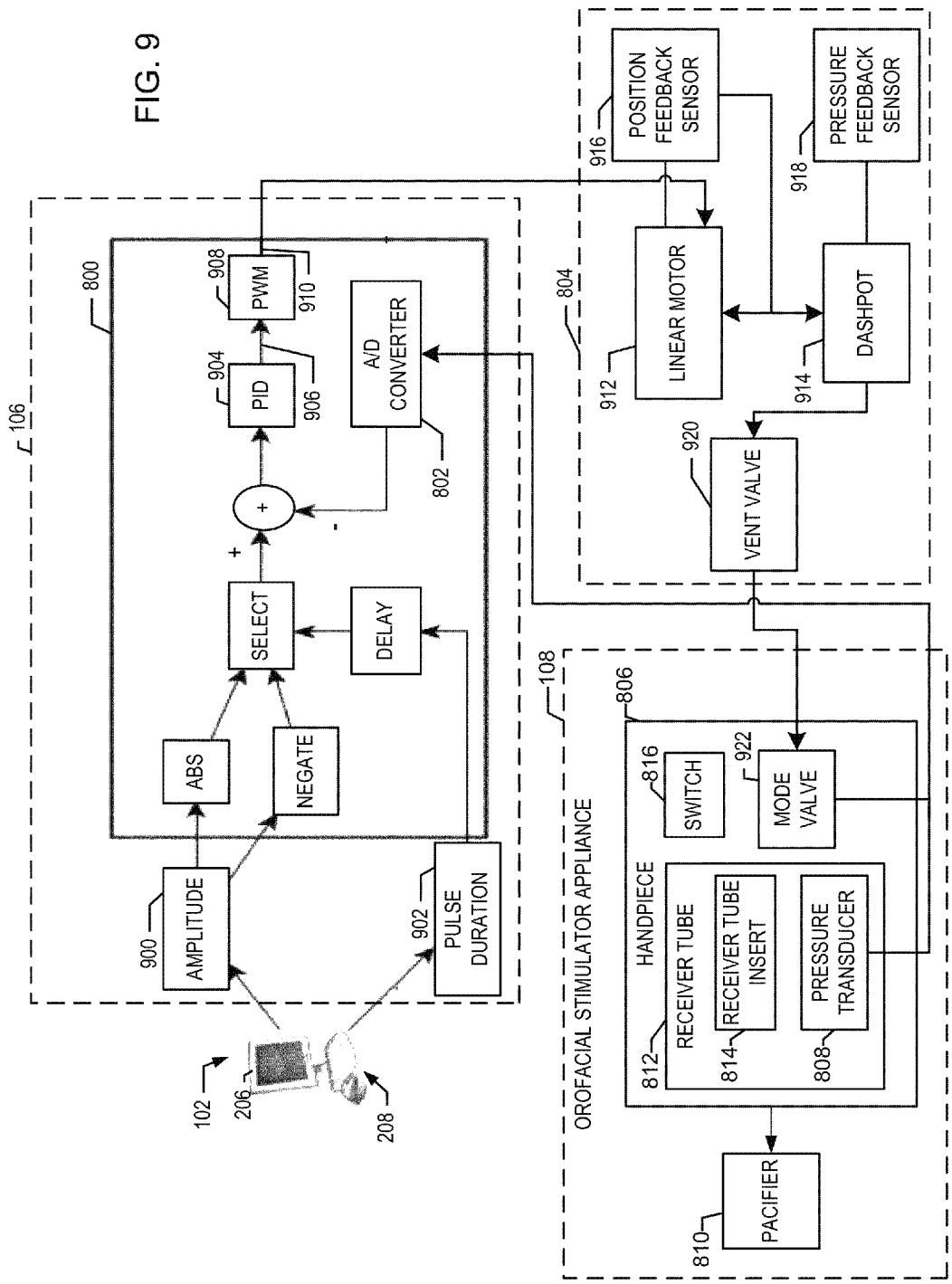

Adding New Patient

Background

| Last | First | Middle | Patient Alias |

Hospital ID   Birthdate   GA at Birth
  11/11/1111   ☐ weeks  ☐ days

Gender
Primary Clinician   Weight (grams)   ○ Male
<unknown>   ○ Female

Assessment Schedule                Therapy Schedule
  0 ☐ Assessments / week             0 ☐ Therapies / day
  0 ☐ Number of weeks                0 ☐ Number of weeks
  0   Number of sessions             0   Number of sessions (?)                          ( Cancel )    ( Save )

Please describe the dominant patient state for the session

Patient State: No Value

Please verify that the completed assessment is assigned to the correct patient

○ correct, assigned to patient: Simpson, Homer

○ incorrect, reassign to patient:

Add optional notes

ENHANCED THERAPEUTIC STIMULUS SYSTEM AND METHODS OF USE

FEDERALLY SPONSORED RESEARCH OR DEVELOPMENT

The subject matter discussed in this patent application was funded in part by United States Grant No. R01-DC003311 from the National Institute of Health (NIH). The government may have certain rights to the subject matter discussed herein.

FIELD OF THE INVENTION

The invention relates generally to systems and methods for stimulating a central pattern generator and a trigeminal nerve in a brain of a human subject. Specifically, the present invention relates to stimulation that influences brain response or brain development including repair of the brain, control of respiration, control of a non-nutritive suck pattern, mastication, and combinations thereof.

BACKGROUND OF THE INVENTION

Premature birth places infants at increased risk for learning disabilities, delayed development of speech, language and motor skills, and mortality. The premature infant often has difficulties with respiration and feeding and therefore may remain in the hospital for prolonged periods of time. The non-nutritive suck (NNS) is a motor behavior that can be observed and used to make inference about brain development and organization in this young population.

Oral stimulation therapy is a common practice, in which feeding therapists manually apply a stimulation using their fingertip. Manually applying stimulation, however, has a number of drawbacks. One such drawback includes the variance in the amount of motion (amplitude) and rhythm (frequency) from therapist to therapist, or even by the same individual. As a result, extensive and costly training and experience are required for a therapist to be proficient at providing manual stimulation and assessment.

In addition, manual stimulation is given essentially blind, as patients can respond by producing a variety of undesirable motor actions, including but not limited to clenching the jaws, tongue compression, tongue thrusting, or other reactions that may be confused with desirable NNS events. As such, it can be difficult to determine if the manual stimulation is beneficial to the patient.

Therefore, a need exists for an automated system and method of using the system to assess a patient's natural NNS pattern and to provide precise and beneficial tactile stimulus to correct and organize the patients NNS pattern.

SUMMARY OF THE INVENTION

The present invention relates to a system having hardware, software, and appliance components for assessing and entraining a behavior in a patient and methods of using the system. In particular, the system relates to the use of specific wave patterns that correspond to action patterns, such that the subject's brain is stimulated. The present invention stimulates the central pattern generator of a subject resulting in a developmental response in the orofacial region. In one aspect, the system is used for stimulating a central pattern generator and a trigeminal nerve in a brain of a human subject. The stimulation influences brain response or development of the brain, including but not limited to the repair of the brain, control of respiration, control of a non-nutritive suck pattern, mastication, and combinations thereof. The system includes an orofacial stimulator appliance that, when actuated in response to a signal, generates a mechanical transfer of energy. The transfer of energy can stimulate the subject's brain. The energy is transferred in at least one burst sufficient to be recognized as a tactile stimulus by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz. The pulses are contacted with the subject for at least two minutes each day and at least twice a day for a minimum of five successive days. The use of a square wave is important.

In one aspect, the system of the present invention uses a bi-directional square wave pattern as an input signal to a patient. For example, the square wave pattern may be applied to the patient where it is perceived as an input or feedback signal which then functions as an artificial stimulator of a central pattern generator within the patient's brain. The square wave pattern therefore resonates with the neural system of the patient.

In another aspect, the system is used for stimulating a central pattern generator and a trigeminal nerve in a brain of a subject. The subject may be an adult, an infant, a stroke patient, or other neurologically deficient patients. The stimulation influences brain response or development of the brain, including but not limited to the repair of the brain, control of respiration, control of a non-nutritive suck pattern, mastication, and combinations thereof. The system includes a control system for generating a pressure pulse signal using a pneumatic pulse generator assembly. Other systems may be used, but a pressure pulse has been shown to be effective. The pneumatic pulse generator assembly can further include a linear motor mechanically engaged to a piston of a pneumatic piston and cylinder assembly, wherein the linear motor exerts force on the piston. The pneumatic piston and cylinder provides a pneumatic pressure pulse to the pliable pacifier through a pneumatic airline in response to the force applied to the piston. The pressure transducer assembly also includes at least one feedback sensor to provide position feedback data and pressure feedback data of the linear motor. Other systems may be used so long as generate a constant, precise, and modifiable pressure pulse to the subject's mouth and lips.

The system further includes, for example, an orofacial stimulator appliance having the pacifier in fluid engagement with a receiver tube. The receiver tube is in fluid communication with the pneumatic airline to provide the pneumatic pressure pulse from the pneumatic piston and cylinder to the pacifier surface. The orofacial stimulator appliance also includes a removable receiver tube insert received in the receiver tube to limit a total volume of air in receiver tube.

The pneumatic pulse generator assembly actuates the orofacial stimulator appliance to generate a mechanical transfer of energy. The energy is transferred in at least one burst sufficient to be recognized as a tactile stimulus recognized by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz. At least six successive bursts are contacted with the subject for at least two minutes, at least twice daily.

In various aspects, the orofacial stimulator appliance further includes a pneumatic pulse generator having a PID controller and a pump. The orofacial stimulator appliance may also include a piezoelectric system. The orofacial stimulator appliance may also be in communication with a control application executable at a processor. The processor may be a part of a computing device further having a display device and an input device.

The orofacial stimulator applicator may further include a handpiece, a receiver tube, a receiver tube insert, and a pacifier or baglet. In addition, the handpiece may include a pushbutton switch in communication with the control application.

The PID controller may be a real-time industrial controller, such as a CompactRIO controller. The pump is a linear motor that may further include a position feedback sensor and a pressure feedback sensor. In addition, the pneumatic pulse generator may be a pneumatic piston and cylinder.

In one aspect, each of the two or more pressure pulses includes a damped harmonic of a base frequency. The damped harmonic for the two or more pressure pulses may be identical or vary in frequency. For example, the two or more pressure pulses may have a damped harmonic oscillator profile having a Q factor greater than or equal to ½.

The system may be used to perform various methods for stimulating a central pattern generator and a trigeminal nerve in a human brain of a subject. The stimulation influences brain response or development of the brain, including but not limited to the repair of the brain, control of respiration, control of a non-nutritive suck pattern, mastication, and combinations thereof. The method includes the steps of contacting the human subject with an appliance to stimulate one or more nerve endings near the subject's mouth, including the facial region proximal to at least one lip and a tongue. The method also includes the steps of actuating the appliance in response to a signal to generate a mechanical transfer of energy. The energy is transferred in at least one burst sufficient to be recognized as a tactile stimulus by the central pattern generator of the brain. Each burst includes at least two square wave pulses of the same amplitude, with the pulse period increasing with each successive pulse to form a decelerating pulse train sequence. The pulses range in frequency between about 1.5 Hz and about 5 Hz.

In various aspects, six bursts of the pulses are contacted with the subject for at least two minutes each day and at least twice a day for a minimum of five successive days. In addition, the square wave pulse may displace a surface of the appliance between about 150 microns and 300 microns or between 260 microns and 300 microns for between about 20 milliseconds and about 50 milliseconds.

In one aspect, the pulses in the burst decelerate. For example, the decelerating pulse train may have period intervals of 510, 526, 551, 580, and 626 ms. Similarly, the pulse spectra may have frequencies of 1.7 Hz, 5.5 Hz, 9.0 Hz, 12.5 Hz, and 16.5 Hz.

The method may also include the steps of stimulating an olfactory or auditory region of the brain. The method may also include generating or projecting sound waves to generate the square wave pulses. Typically, the tactile stimuli provided by the method are above any background activity of the subject and the signal to generate the mechanical transfer of energy is a high velocity signal. In various aspects, the method may be formed on infants with a heart defect or on stroke patients. Related objects and advantages of the present invention will be apparent from the following description.

DESCRIPTION OF FIGURES

FIG. 6 is a block diagram of an assessment module according to one aspect of the therapeutic stimulus system.

FIG. 7 is a block diagram of a therapy module according to one aspect of the therapeutic stimulus system.

FIG. 8A is a block diagram of a therapeutic pulse generation system according to one aspect of the therapeutic stimulus system.

FIG. 8B is a block diagram of an orofacial stimulator appliance according to one aspect of the therapeutic stimulus system.

FIG. 9 is a block diagram of a therapeutic stimulus system according to one aspect.

FIGS. 12-31 are screenshots of various graphic user interface displays according to aspects of the therapeutic stimulus system.

DETAILED DESCRIPTION OF THE INVENTION

The present invention relates to a system for assessing and the neural entrainment of a patient. In one aspect, the patient may be a premature infant; however, the system may also be used for patients unable to properly suck or swallow to receive nourishment, including but not limited to full-term infants, toddlers, adolescents, and adults. For example, the system may be used to treat those that have been debilitated by strokes, hemorrhages, heart defects, or other conditions that correlate with an impairment in neurological development or function.

In one aspect, the system of the present invention uses a bi-directional square wave pattern as an input signal to a patient. For example, the square wave pattern may be applied to the patient where it is perceived as an input or feedback signal which then functions as an artificial stimulator of a central pattern generator within the patient's brain. The square wave pattern therefore resonates with the neural system of the patient.

The non-nutritive suck (NNS) pattern of a patient is generated by the patient's suck central pattern generator (sCPG). A central pattern generator (CPGs) is a neural circuit or combination of neural circuits located in the patient's cerebral cortex, brainstem, and/or spinal cord that drives rhythmic motor behaviors such as sucking, breathing, mastication, and locomotion. The patterns generated by the CPGs can be modulated by a variety of external stimuli, such as the square wave pattern of the present invention. In particular, the square wave pattern may be applied to the mouth and lips of a patient where the tongue functions as a high-pass filter to permit components of the square wave pattern matching a natural oscillation pattern of the sCPG to stimulate the patient's sCPG. As such, the most beneficial therapeutic results are manifested when the therapy consistently mimics the intrinsic frequency of sCPG.

It is often difficult for therapists to model the fine temporal structure of an organized NNS burst pattern, which involves a frequency-modulated (FM) burst structure, using manual stimulation. The FM burst structure is characterized by a series of suck cycles that successively decrease in frequency from the first compression cycle of the lips and mouth to the last compression cycle. The FM burst structure typically modulates between 1.5 Hz and 3 Hz. The structure of the FM burst is very difficult if not impossible to produce manually in a repeated pattern by even the most experienced therapist.

The present invention relates to the identification of particular characteristics of the FM burst structure and provides criteria or descriptions of features of the NNS pattern that may be used as diagnostic indicators for gauging the development of oromotor control among patients. Further, the identified characteristics may be useful in configuring a tactile stimulus that may be applied to patients to modify or correct a deficient NNS pattern.

The Therapeutic Stimulus System

Figure 1:
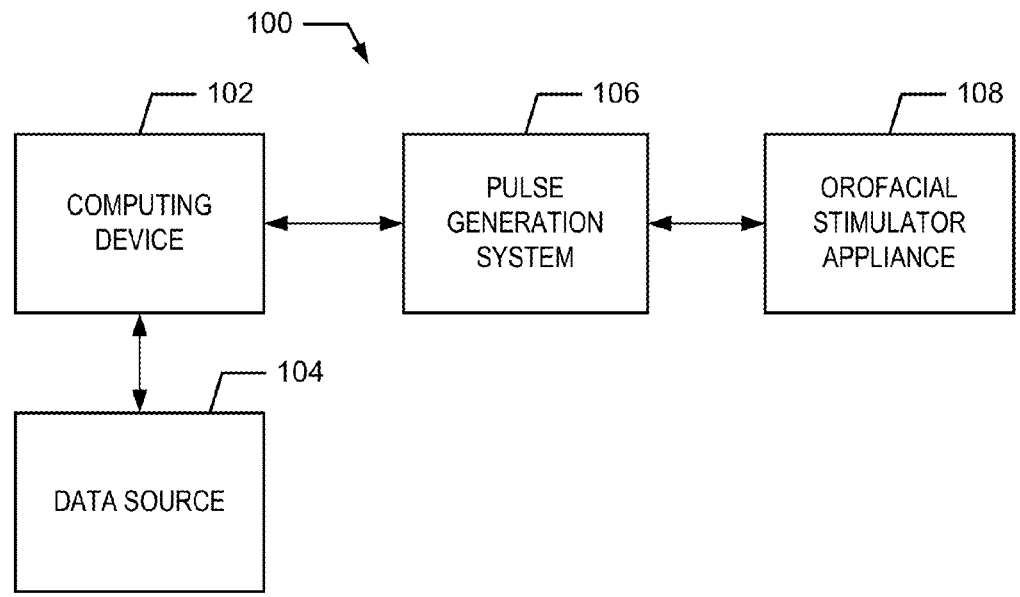
FIG. 1 is a block diagram of a therapeutic stimulus system according to one aspect.

FIG. 1 is a block diagram of a therapeutic stimulus system 100 for assessing a patient's neuromuscular behavior and for providing a tactile stimulus that will stimulate a central pattern generator (CPG) and trigeminal nerve of a human brain to entrain a desired neuromuscular pattern. The therapeutic stimulus system 100 may be used to assess and entrain brain activity for controlling respiration, mastication, other neuromuscular functions, or combinations thereof. For example, the therapeutic stimulus system 100 may be used to treat patients suffering a stroke or other conditions that prevent the patient from performing a desired function. The therapeutic stimulus system 100 includes a computing device 102 to process data and execute one or more applications, a data source 104 to store data, a pulse generation system 106 to generate pneumatic pulses in response to input signals, and an orofacial stimulator appliance 108 to transfer the pneumatic pulses to a patient as a tactile stimulus.

According to one aspect, the therapeutic stimulus system 100 can be used for assessing a patient's natural non-nutritive suck (NNS) pattern and for providing a tactile stimulus that will stimulate the suck central pattern generator (sCPG) and trigeminal nerve of the patient's brain to entrain a proper NNS pattern.

Figure 2:
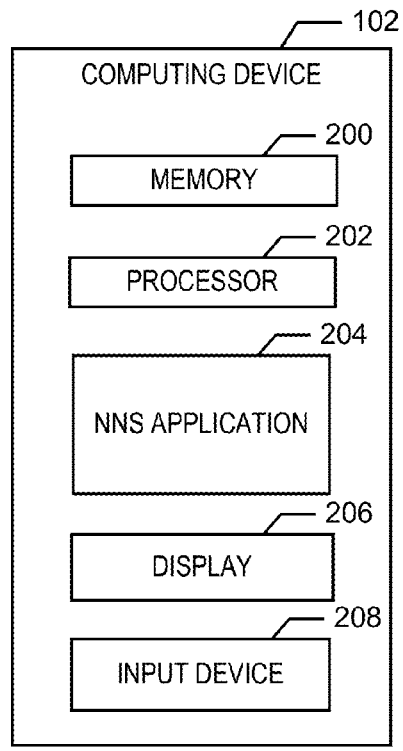
FIG. 2 is a block diagram of computing environment according to one aspect of the therapeutic stimulus system.

By way of example and not limitation, the computing device 102 may include memory 200 and at least one processor 202 to execute a NNS assessment and therapy application (NNS application) 204, as shown in FIG. 2. The computing device 102 also includes a display 206, such as a computer monitor, for displaying data stored in the data source 104, data received from the pulse generation system 106 or the orofacial stimulator appliance 108, and data input by a user of the therapeutic stimulus system 100. The display device 206 also displays one or more graphical user interfaces (GUIs) input forms or displays, generated by the NNS application 204, as shown in FIGS. 12-31. The GUI input forms and displays enable a user of the therapeutic stimulus system 100 to input, view, and/or interact with the various modules of the system. The GUI input forms and displays also allow a user to input, view, and/or interact with patient data, NNS assessment data, NNS therapy data, and/or other data related to the assessment and therapeutic stimulation of the patient. Further, the GUI input forms and displays permit a user to configure and interact with the pulse generation system 106 and the orofacial stimulator appliance 108.

The computing device 102 may also include an input device 208, such as a keyboard or a pointing device (e.g., a mouse, trackball, pen, or touch screen) to enter data or configure a feature of the therapeutic stimulus system 100 using the GUI input forms and displays. The computing device 102 may further include, or at least be in communication with, the data source 104.

The data source 104 may be a database stored on a local hard disk drive (HDD) incorporated into the computing device 102. Alternately, the data source 104 may be a database or other data structure stored remotely from the computing device 102. For example, the computing device 102 may be in communication with the data source 104 over a network, including but not limited to the Internet. As shown in FIG. 7, the data source may store a variety of data. For example, the data source 104 may store user data 700 that includes profiles and login information, such as passwords, for users of the therapeutic stimulus system 100. The data source 104 may also contain patient data 702 including patient charts and historical assessment and therapy session data 704 and 706, respectively. The data source 104 also stores data for therapy protocols or therapy pulse profiles 708 that may be used to entrain a variety of patients, as well as, other data 710 gathered from experiments or research trials conducted using the therapeutic stimulus system 100.

Figure 3:
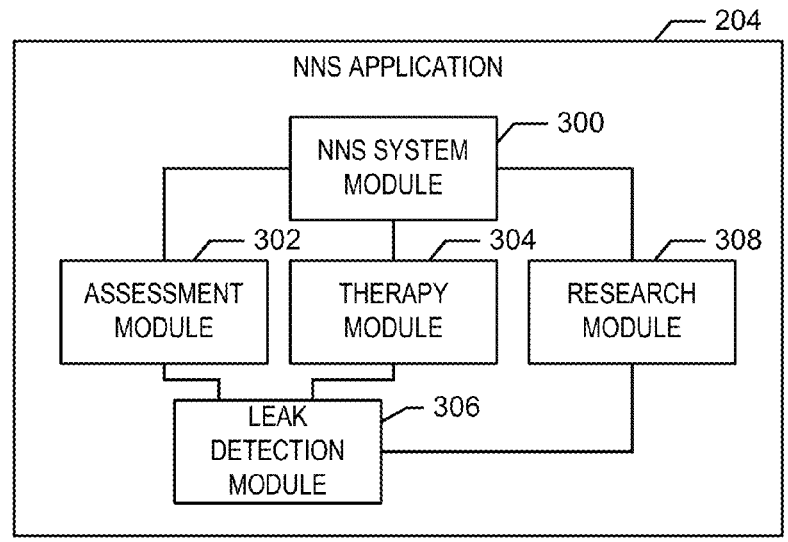
FIG. 3 is a block diagram of data source according to one aspect of the therapeutic stimulus system.
Figure 4:
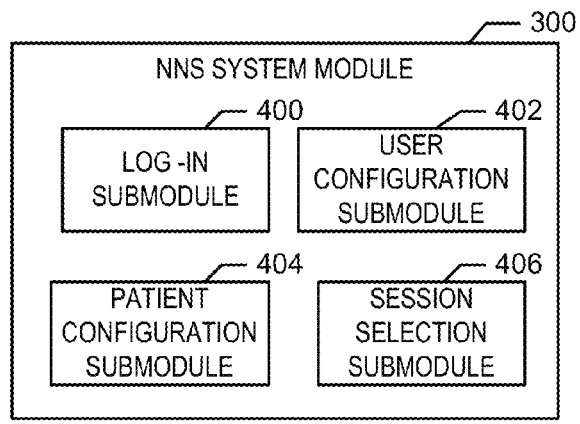
FIG. 4 is a block diagram of a non-nutritive suck entrainment application according to one aspect of the therapeutic stimulus system.
Figure 5:
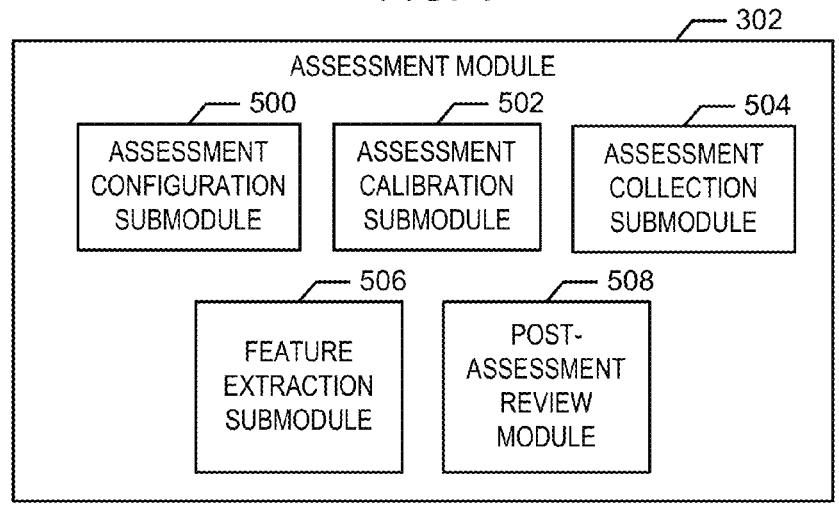
FIG. 5 is a block diagram of a system module according to one aspect of the therapeutic stimulus system.

According to one aspect, as shown in FIG. 3, the NNS assessment and therapy application 204 includes a number of instructions, applets, modules 300-308, and submodules to receive, process, and generate data and/or signals for the assessment of a NNS pattern and the therapeutic stimulation of a patient's mouth and lips to entrain a proper NNS pattern. The modules of the NNS assessment and therapy application 204 include an NNS system module 300, an assessment module 302, a therapy module 304, a leak detection module 306, and a research module 308.

Figure 12:
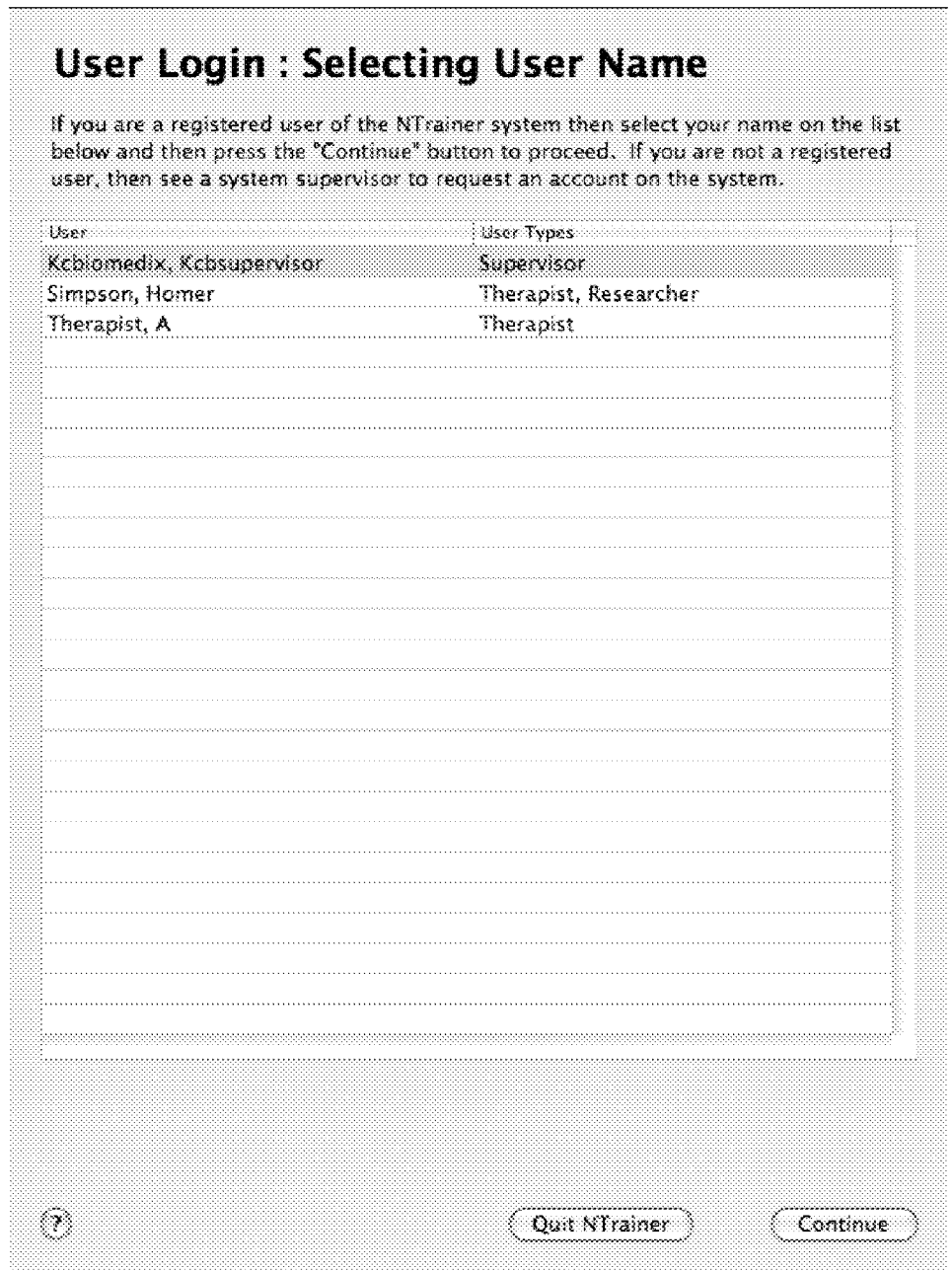
Figure 13:

The NNS system module 300 includes various submodules 400-406 to provide access to various the features and functionality of the NNS assessment and therapy application 204. For example, the NNS system module 300 includes a user login submodule 400 that allows a user of the therapeutic stimulus system 100 to login into the NNS application 204. In one aspect, the NNS system module 300 generates GUI input forms 1200 and 1202, as shown in FIGS. 12-13, where the user may select a user account and log in to the NNS application 204 after entering a valid password for the selected user.

Figure 14:
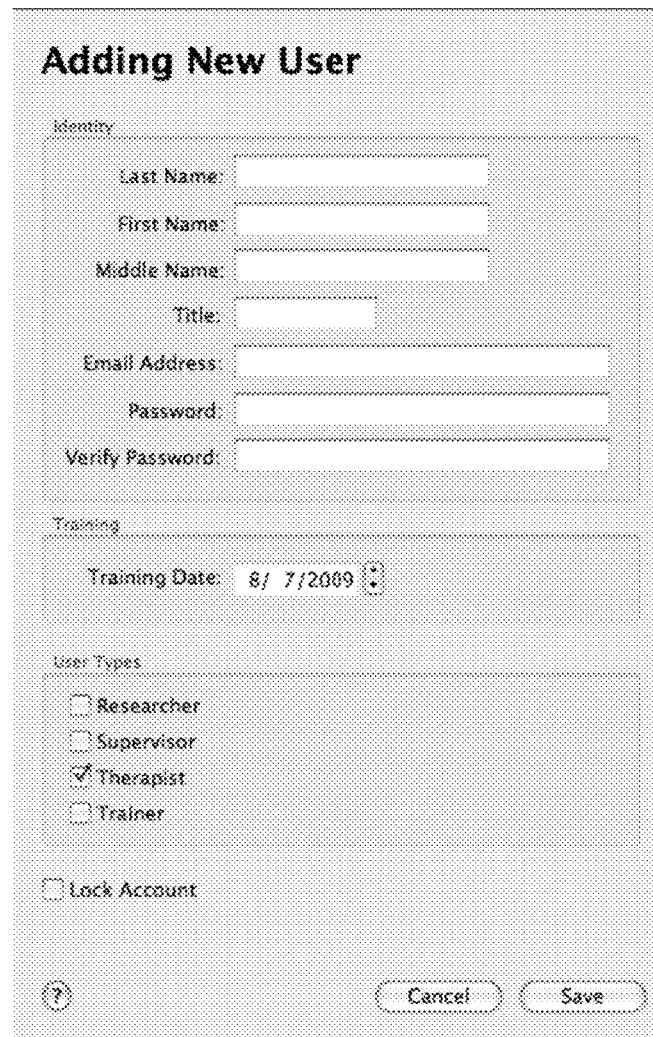
Figure 15:
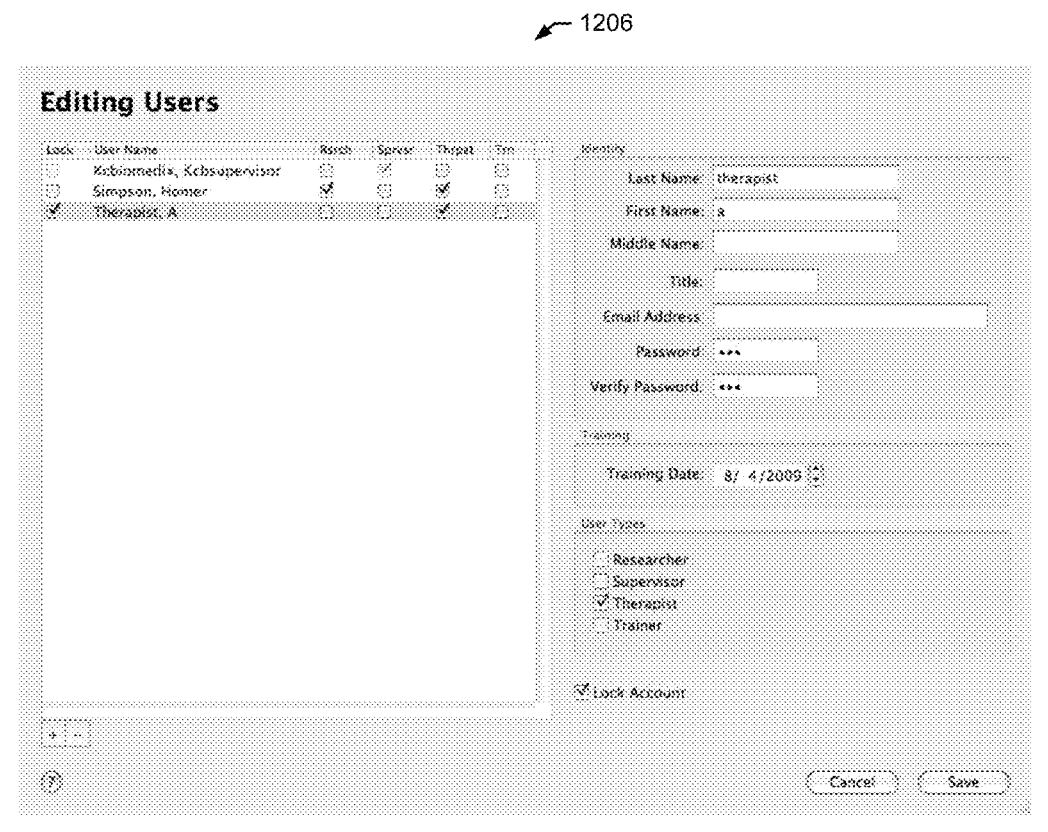

The NNS system module 300 includes a user configuration submodule 402 that allows users of the therapeutic stimulus system 100 with sufficient privileges to add, edit, or delete user accounts. By way of example and not limitation, an administrator may input data into GUI input forms 1204 and 1206, as shown in FIGS. 14-15 to create, modify, or delete a user profile to grant or restrict access to the NNS application 204.

Similarly, the NNS system module 300 includes a patient configuration submodule 404 that allows users of the therapeutic stimulus system 100 with sufficient privileges to add, edit, or delete patients. By way of example and not limitation, an administrator may input data into input forms 1208 and

Figure 17:

1210, as shown in FIGS. 16-17, to create, modify, or delete a profile for a patient that may receive an NNS assessment or therapy using the therapeutic stimulus system 100. The NNS system module 300 also includes a session selection submodule 406 that allows users of the therapeutic stimulus system 100 to select whether the NNS system will be used to assess a patient's naturally generated NNS pattern or to provide therapeutic stimulus to the patient. As such, the session selection submodule 406 sends requests to the assessment module 302 and the therapy module 404 in response to type of session selected by the user.

Figure 18:
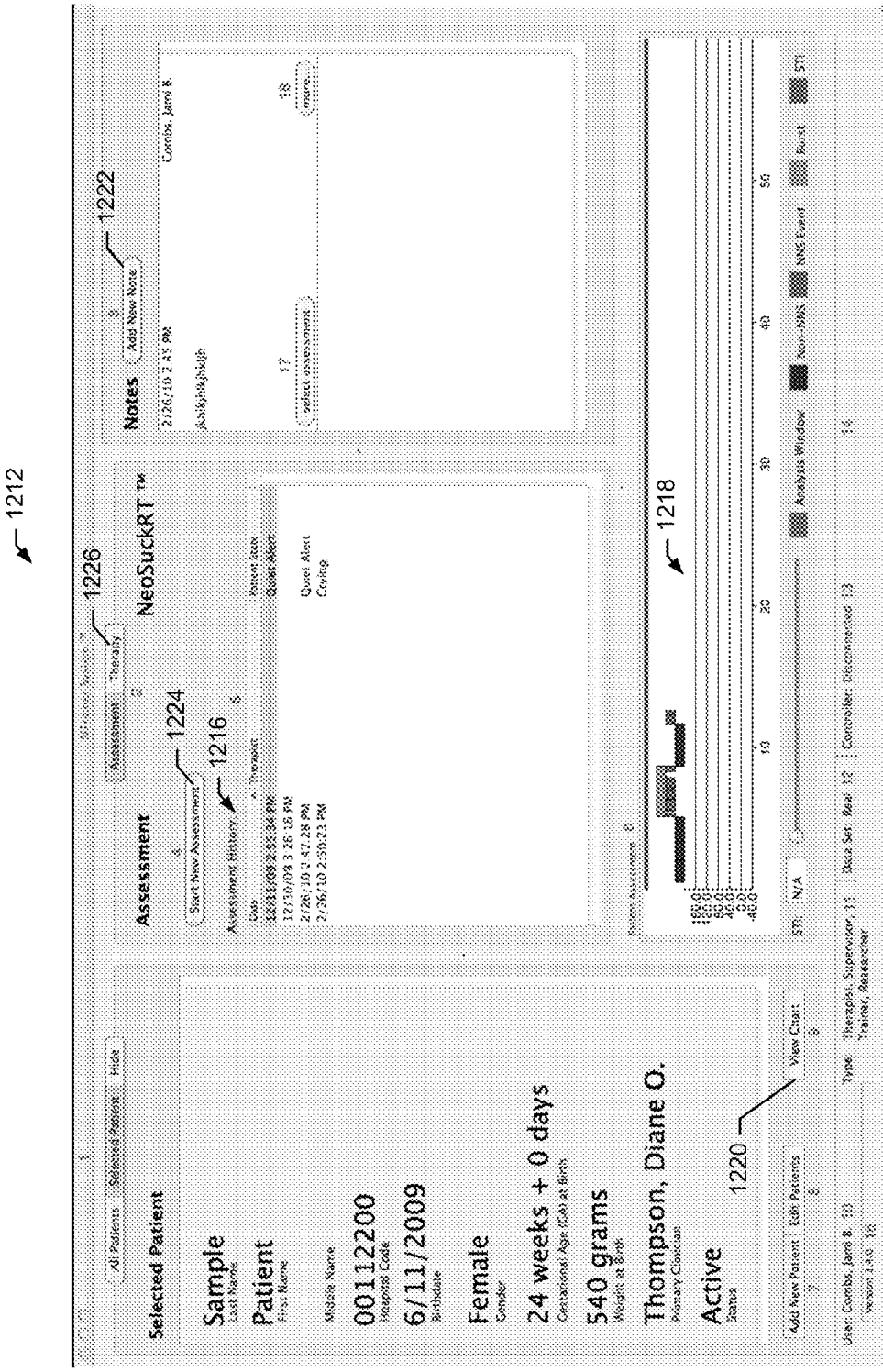
Figure 19:
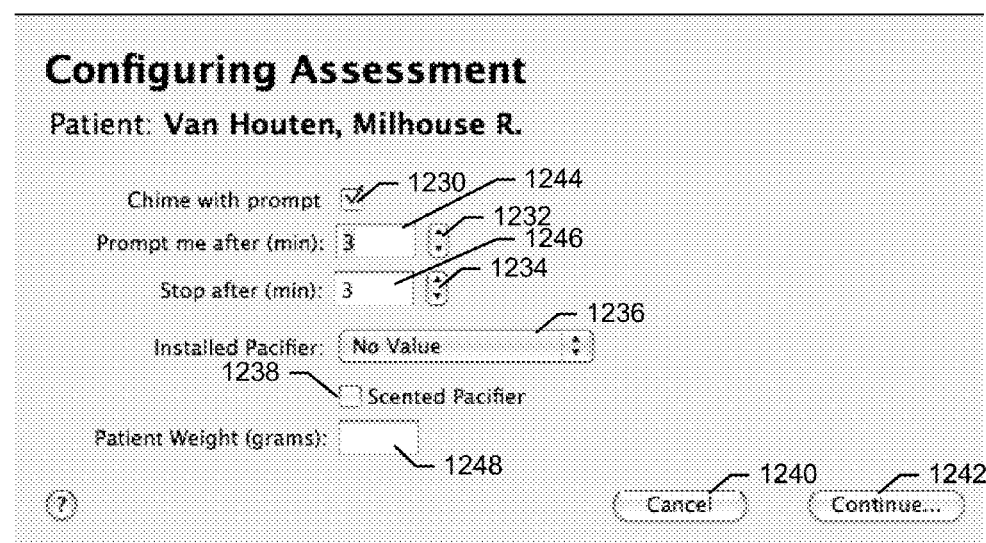
Figure 20:
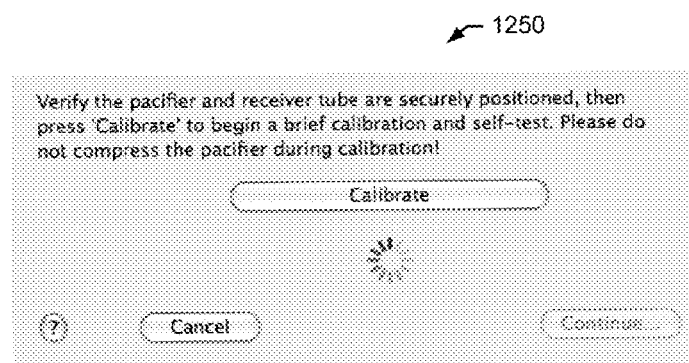
Figure 21:
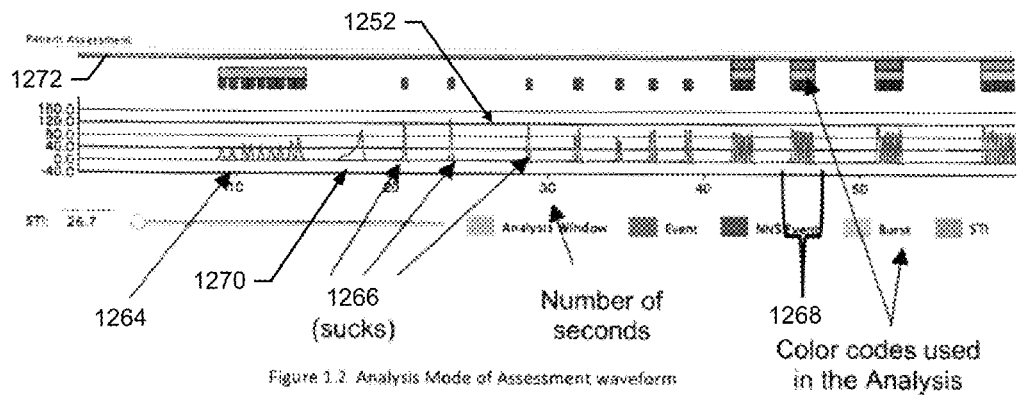
Figure 22:
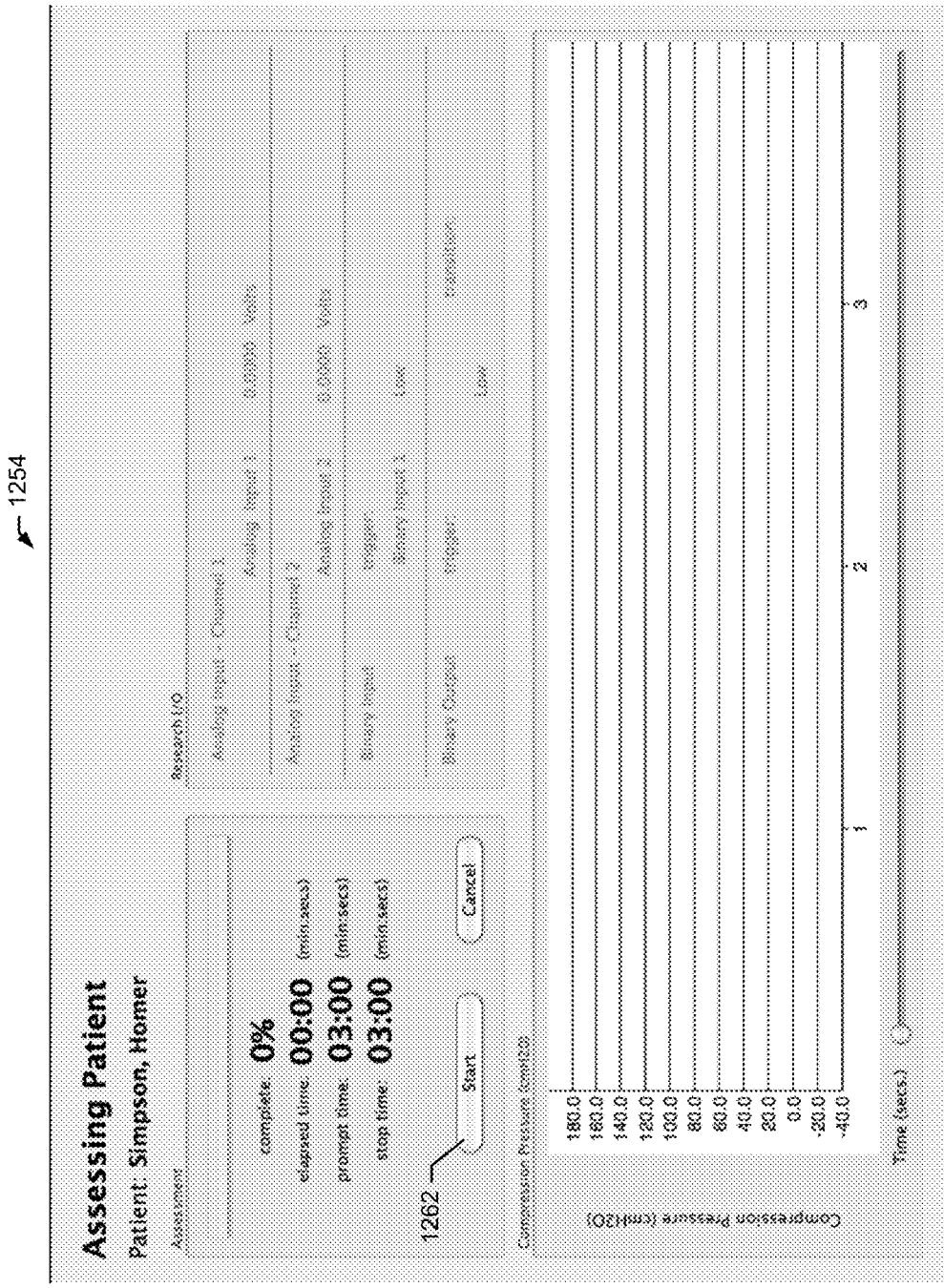
Figure 23:
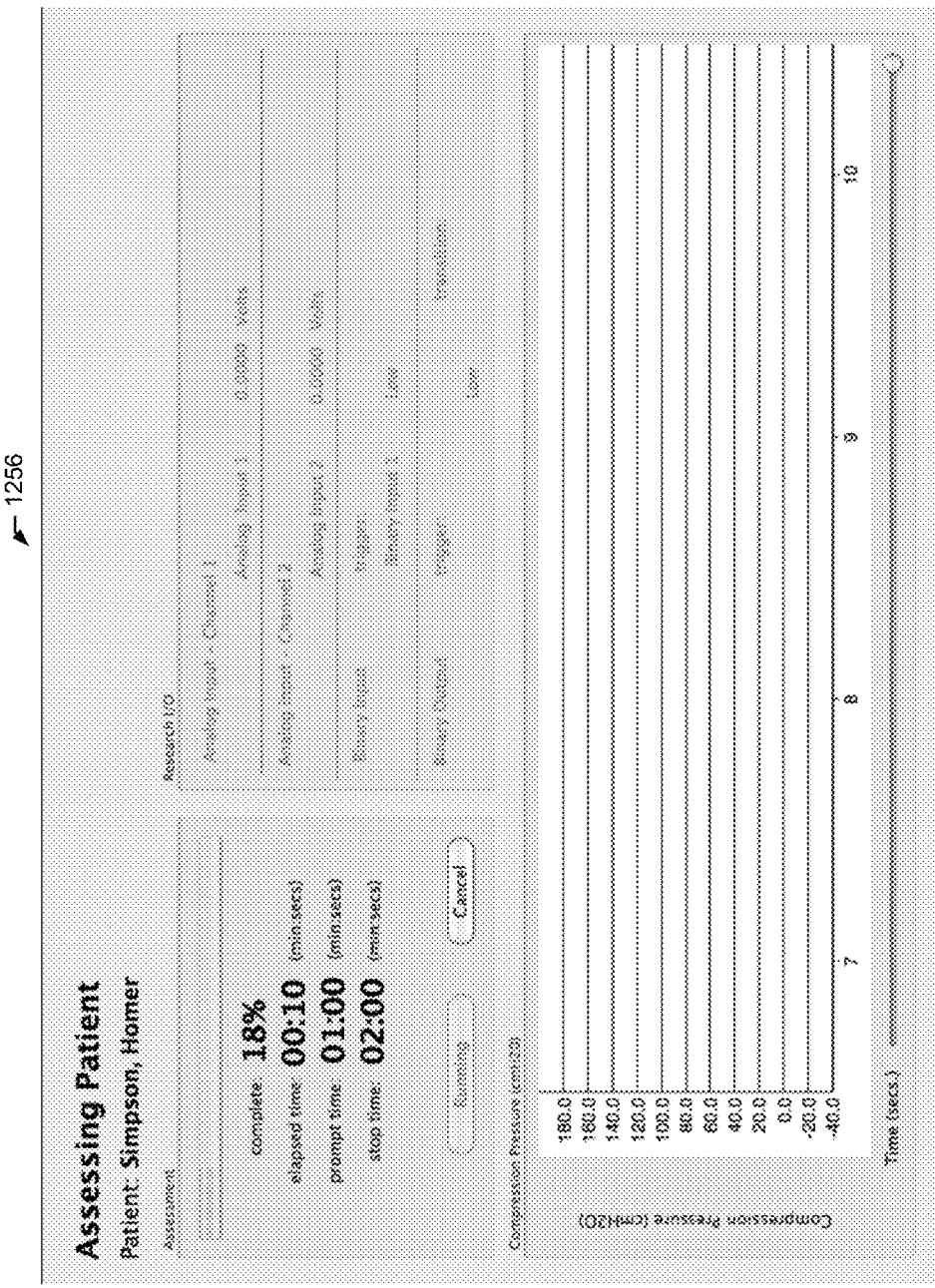
Figure 24:
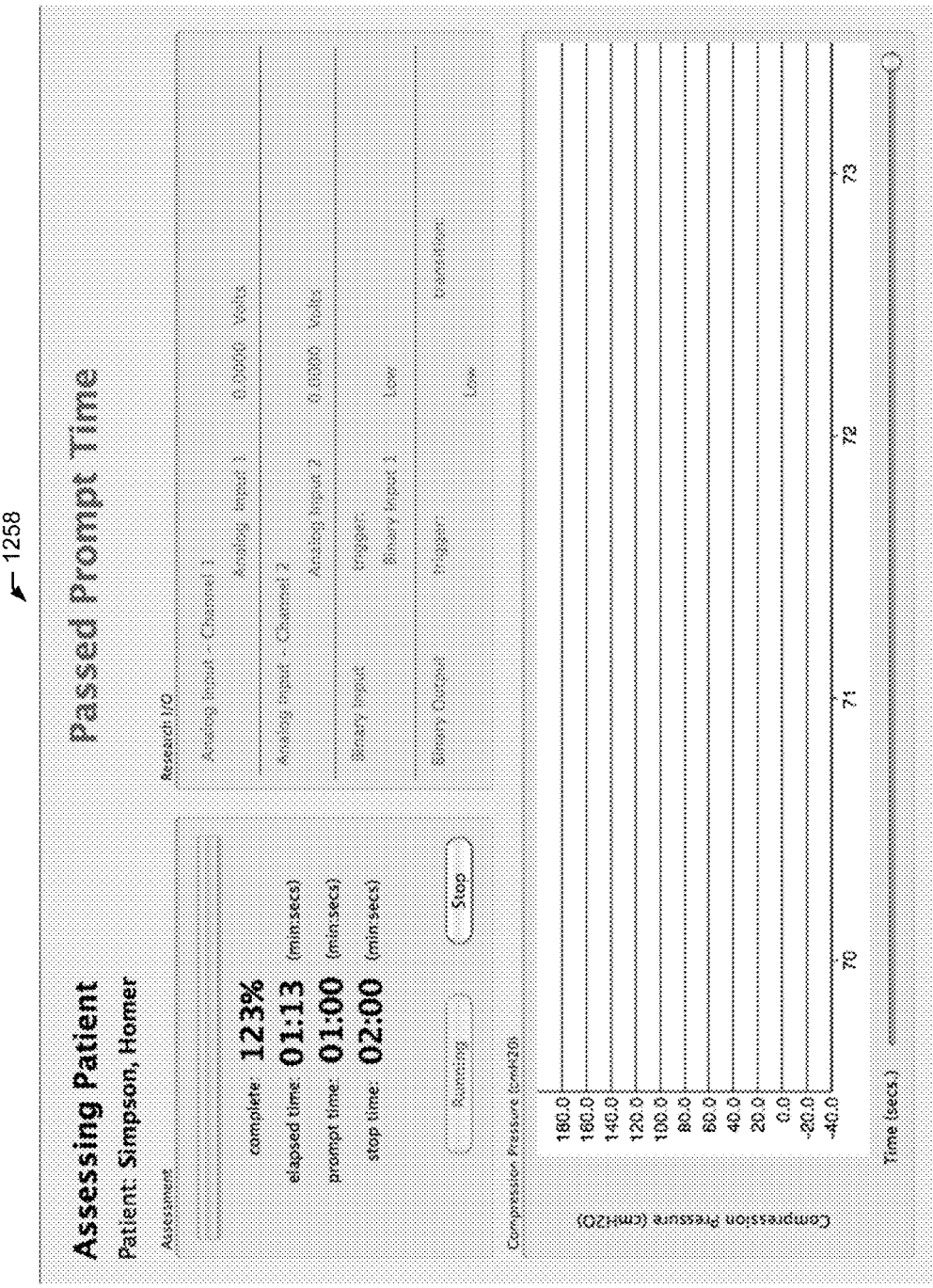
Figure 25:
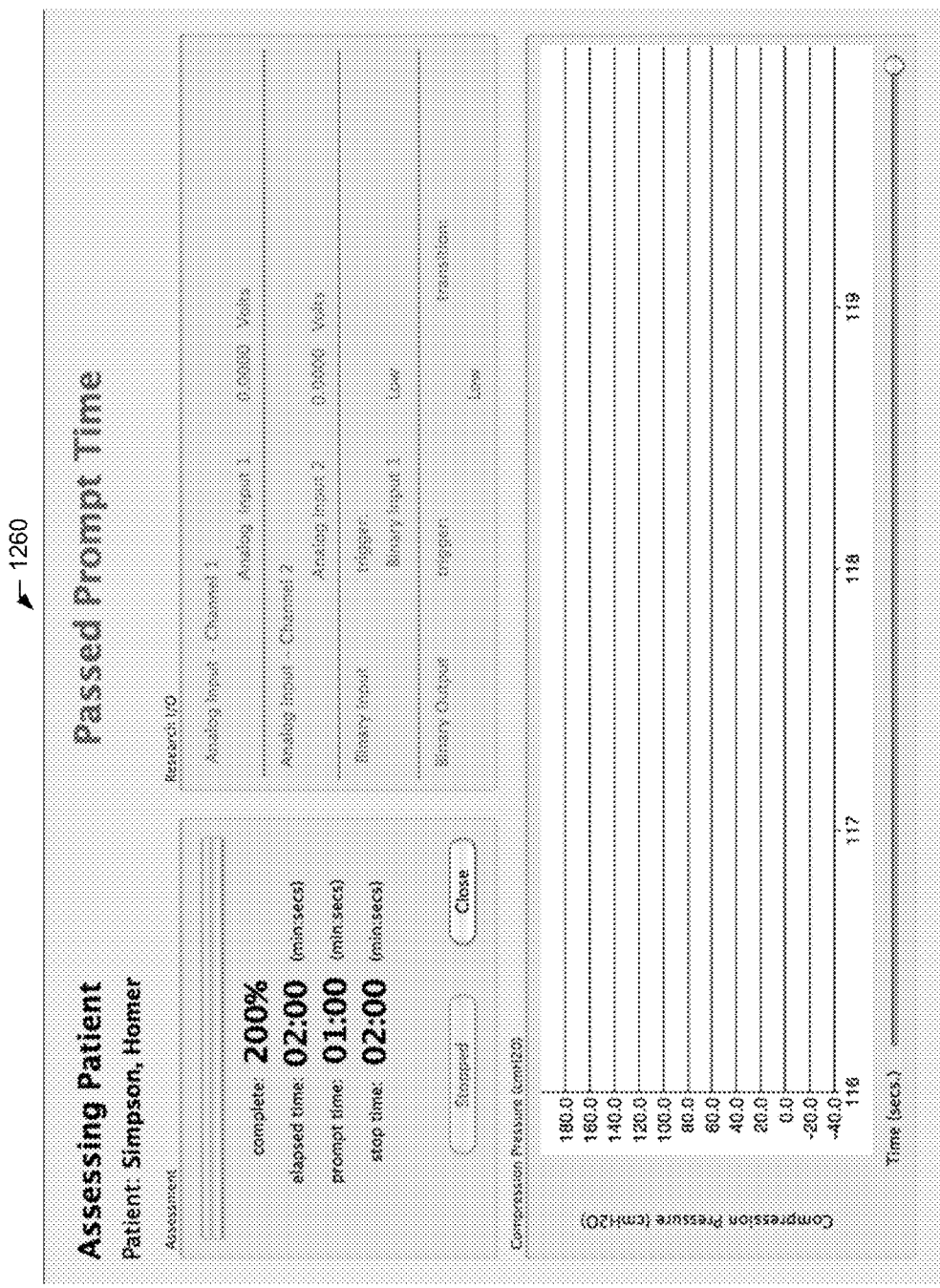
Figure 28:
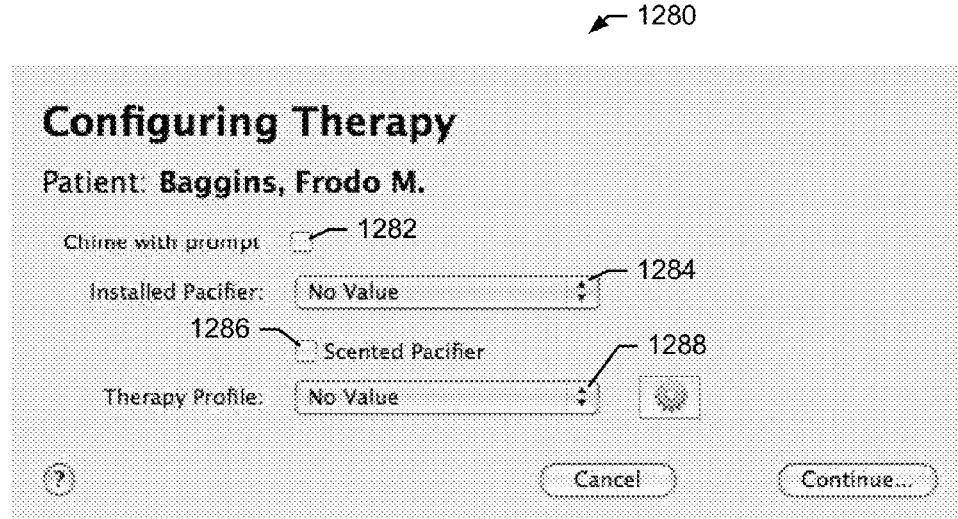

When an assessment request is generated, the NNS system module 300 generates a main assessment input form 1212 to allow the user to input data and interact with the NNS application 204 during the assessment session. By way of example, and not limitation, an embodiment of the main assessment input form 1212 is shown in FIG. 18. In one aspect, the main assessment input form 1212 includes one or more control buttons 1214 to access a list of all the patients actively associated with the NNS application 204. When a patient is selected, the main assessment input form 1212 displays a history 1216 of assessments for the selected patient, and is capable of displaying waveforms from the previous assessments in a waveform frame 1218. In one aspect, the prior waveforms and assessment histories 1216 may be stored as assessment session data 704 in the data source 104.

Figure 31:
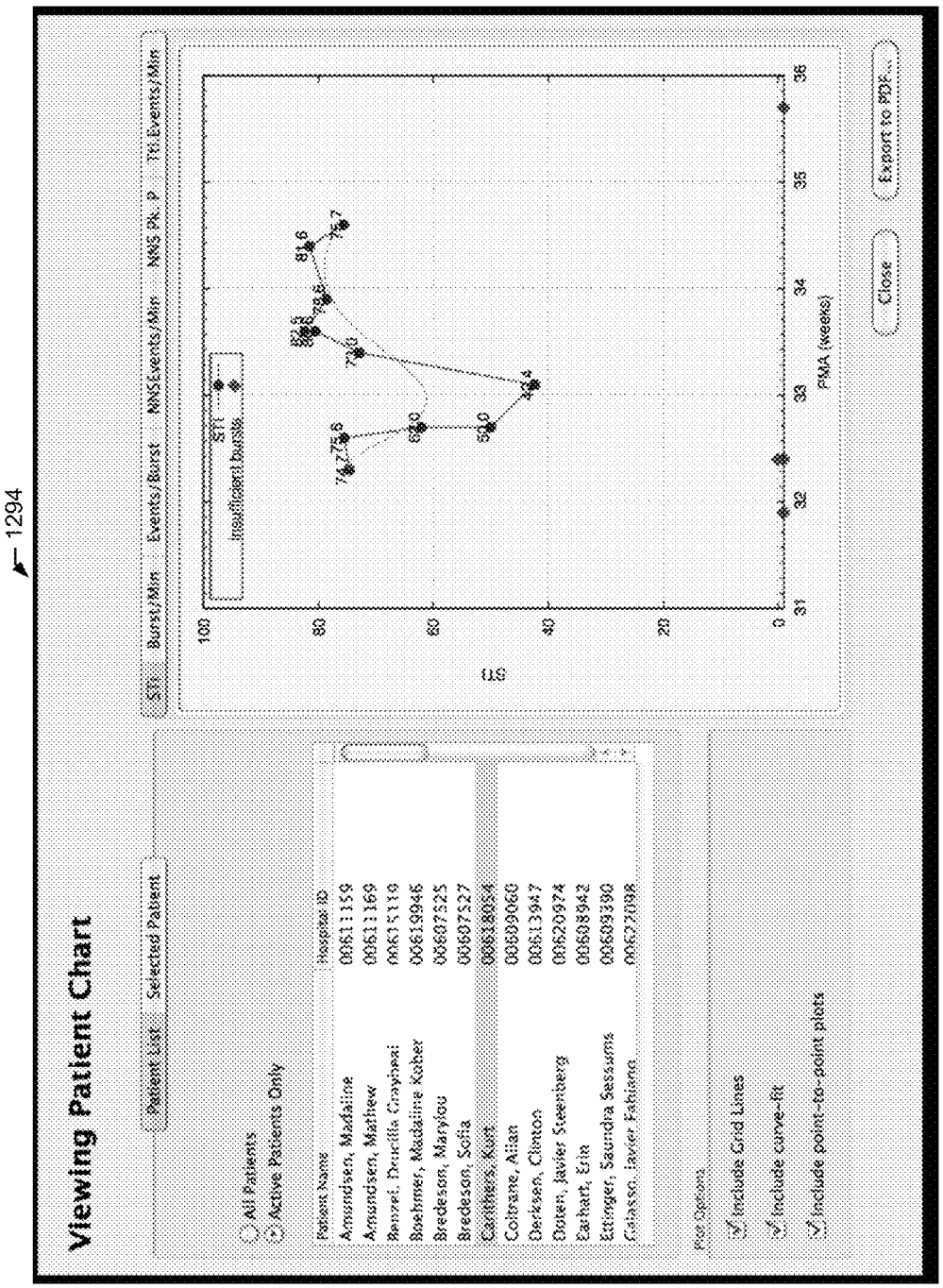

The main assessment input form 1212 also includes a control button 1220 to permit a user to view a patient's medical chart 1294, an example of which is shown in FIG. 31. In addition, the control button 1220 allows the user to add or edit patient data, while control button 1222 allows the user to add notes to the patient assessment data. In addition, the user may select control button 1224 to start a new assessment session for the selected patient or select control button 1226 to switch directly to a therapy session for the selected patient.

In one aspect, the assessment module 302 includes a number of submodules 500-508, including but not limited to an assessment configuration submodule 500, an assessment calibration submodule 502, an assessment capture module 504, a feature extraction submodule 506, and a post-assessment review module 508. The various submodules 500-508 generate and display one or more GUI input forms as shown in FIGS. 19-26 that allow the user to configure, initiate, and review an assessment session.

The assessment configuration submodule 500, for example, generates an assessment configuration GUI input form 1228. The assessment configuration GUI input form 1228 includes one or more controls 1230-1242 and data fields 1244-1248 to input data for selecting or configuring an assessment session. The input data may relate to a total assessment time 1246, an intermediate assessment prompt 1244, a type and configuration 1236 of a baglet or pacifier 810, and optionally, the patient's weight 1248. As the behavior and mood of a patient is often unpredictable, it is difficult for the user to know in advance how long the assessment session may take. Therefore, the intermediate assessment prompt is selected as a 'best estimate' for the actual time that it may take to capture enough NNS pattern activity to assess the patient. As such, the total assessment time permits the user to continue to collect data, if desired, after the intermediate assessment prompt. In one aspect, the assessment collection submodule 504 halts the capture of assessment data at the intermediate assessment prompt.

The assessment calibration submodule 502 generates an assessment calibration GUI input form 1250. In one aspect, the calibration input form 1250 allows the user to communicate with and configure the pulse generation system 106 and the orofacial stimulator appliance 108 to verify the intended function and calibration for the components of the pulse generation system and the orofacial stimulator appliance prior to the initiation of an assessment session.

The assessment capture submodule 504 receives the digital pressure signal from the pulse generation system 106. In one aspect, the assessment capture submodule 504 records and displays the patient's NNS pattern activity as a waveform 1252. In other aspects, the assessment capture submodule 504 may receive and store the digital pressure signal without displaying the NNS pattern activity. In another aspect, the assessment capture submodule 504 may display the NNS pattern activity in another form, such as a chart, graph, or table.

The assessment capture submodule 504 may further generate a number of displays during the assessment capture session. For example, FIGS. 22-25 are screen displays that show the progress of the assessment session at the start of the session 1254, at the intermediate prompt interval 1256, at the user input duration time 1258, and at the conclusion of the assessment session 1260. In other aspects, fewer or a greater number of displays 1254-1260 may be provided during the assessment session.

In one aspect, the assessment data capture session may be initiated by input received through a start control button 1262 shown on the display 206. Alternately, the assessment data capture session may be initiated by a switch on a handpiece 806 of the orofacial stimulator appliance 108.

During or subsequent to an assessment session, the feature extraction submodule 506 analyzes the digital pressure signal received by the assessment capture submodule 504. In particular, the feature extraction submodule 506 identifies various components of the patient's generated NNS pattern. For example, in the waveform 1252 of FIG. 21, the feature extraction submodule 506 identifies pressure peaks 1264, individual suck events 1266, as well as bursts 1268, which are defined as two or more suck events in less than about 1.2 seconds. In addition, the feature extraction submodule 506 also identifies a number of non-NNS events 1270, such as chewing motions made by the patient. In one aspect, the feature extraction submodule 506 may provide annotations, including color-coding, to identify the various NNS events 1264-1268.

In one aspect, the feature extraction submodule 506 quantifies the overall performance of the patient's generated NNS pattern by assigning a Spatiotemporal Index (STI) value to the pattern. For example, the STI value may be derived by calculating the similarity of up to five individual suck bursts. The STI value measures the symmetrical and repetition of the patient's generated NNS burst pattern by integrating the symmetry and quantity of selected NNS events 1264-1268 in the patient's NNS pattern.

In another aspect, the feature extraction submodule 506 automatically determines a number of parameters that are desirable for evaluating the patient's generated NNS pattern and determining the best course of therapy to treat the patient. For example, the evaluation parameters may include the STI value for the waveform, the number of bursts per minute, the number of events per burst, the number of NNS events per minute, an average peak pressure, as well as the total number of events per minute. In other examples, a fewer or greater number of parameters as well as different parameters may be considered when evaluating the patient's generated NNS pattern.

The evaluation parameters may be determined using a portion or subset of the collected assessment data. For example, a "most active" two-minute window having the most number of NNS events is identified by the feature extraction submodule 506. The most-active window is generally indicated by a bar 1272 on the displayed waveform 1252. When calculating the six evaluation parameters, the feature extraction submodule 506 may ignore any NNS activity outside of the most-active window.

After capturing the patient's generated NNS pattern and determining the evaluation parameters, the post assessment review module 508 generates a post-session GUI input form 1274 where the user may confirm the identity of the patient that underwent the assessment session and input notes regarding the assessment session. By way of example and not limitation, the user may indicate the state of alertness for the patient, by inputting terms such as alert, crying, drowsy, sleepy, or any other term that identifies the patient's level of alertness during the assessment session. The user may further quantify the patient's state of alertness as active or quiet, as the patient's STI value may fluctuate between assessment sessions due to the patient drifting off to sleep during the capture period.

Once a patient has been diagnosed or characterized as having a disorganized NNS pattern, it is often desirable for the patient to undergo a therapy session to entrain the patient's sCPG to produce an organized NNS pattern. Typically, a therapy session consists of applying an external stimulus to or near the lips and mouth of the patient in order to modify the NNS pattern generated by the sCPG. The orofacial stimulator appliance 108 contacts the patient on or near the lips and mouth to deliver therapeutic stimulation, provided by the pacifier's motion as caused by the pressure pulses, to the patient's orofacial nerves via regulated changes in the surface diameter of a pacifier 810 that is a component of the orofacial stimulator appliance 104, as shown in FIGS. 8B and 9. The pressure pulses conveyed by the orofacial stimulator appliance 108 are actuated at the pulse generator or pulse transducer system 104 in response to a therapy pulse profile generated by the therapy module 304.

Figure 27:
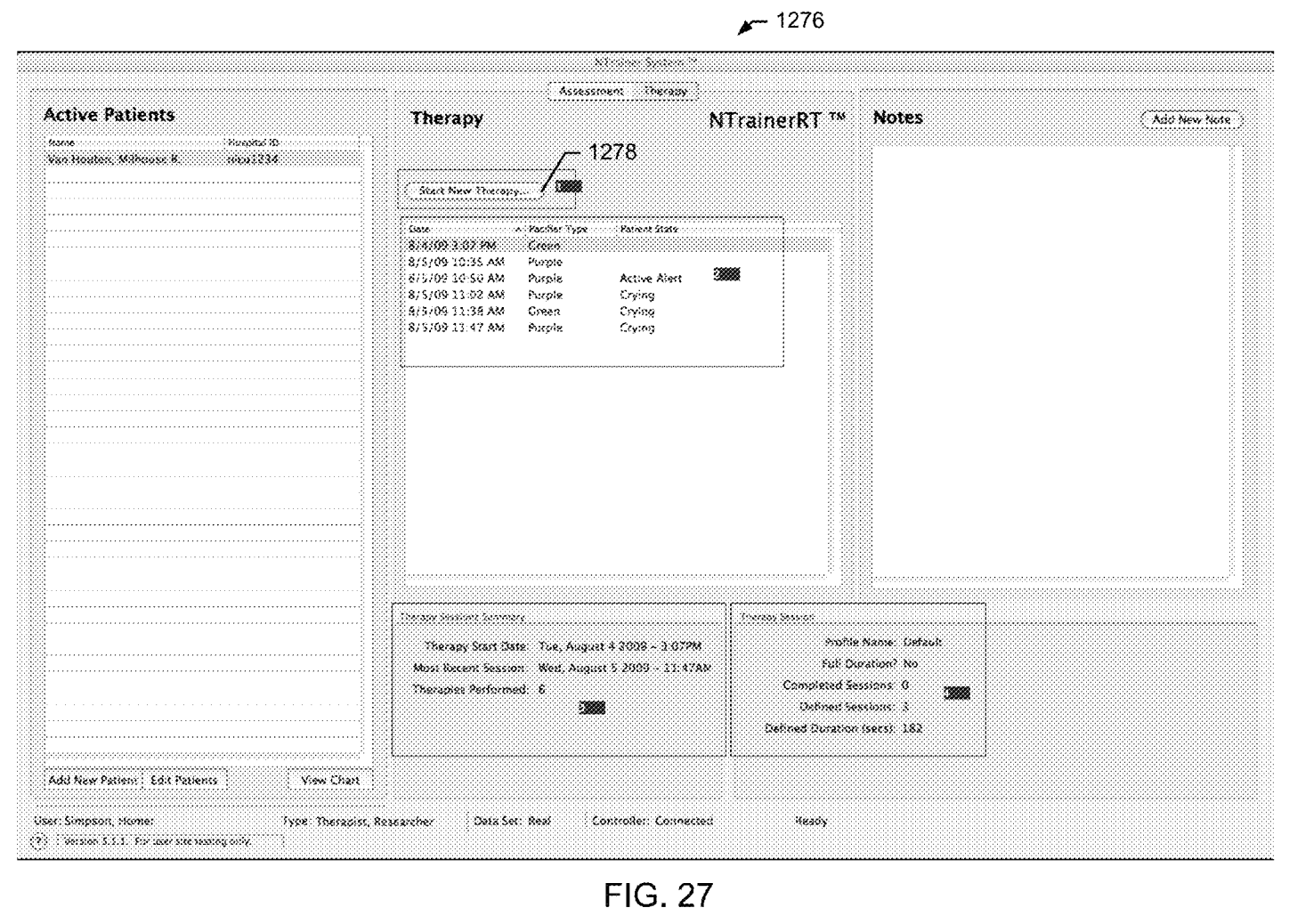

When a therapy session is to be performed, the NNS system module 300 generates a main therapy GUI input form 1276, as shown in FIG. 27. The main therapy GUI input form 1276 includes a control button 1278 to allow a user to start new therapy session. The main therapy GUI input form 1276 also includes a control button to display previous therapy session data 706 stored in the data source 104, the therapy sessions data 706 includes summaries and detailed information for previous therapy sessions.

In one aspect, the therapy module 304 includes a number of submodules 600-606, including but not limited to a therapy configuration submodule 600, a therapy calibration submodule 602, a therapy execution submodule 604, and a post-therapy review submodule 606. The various submodules 600-606 generate one or more GUI input forms for display that allow the user to configure, execute, and review a therapy session.

The therapy configuration submodule 600, for example, generates a therapy configuration input form 1280. The assessment configuration GUI input form 1280 includes a number controls 1282-1286 related to the therapy session and the pacifier 810 of the orofacial stimulator appliance 108. The assessment configuration GUI input form 1280 also includes a control button 1288 that allows the user to select or modify one or more therapy pulse profiles.

A therapy pulse profile consists of one or more therapeutic waveforms that result in variable but controlled radial displacements of the outer surface of the pacifier 810. The surface displacements of the pacifier 810 provide a tactile stimulus to or near the lips and mouth (e.g., intraoral, anterior tongue tip, anterior tongue dorsum) of the patient to entrain the patient's sCPG to naturally produce an NNS pattern that mimics the generated therapy waveforms. Once configured, the therapy waveforms are actuated by the pulse generation system 106, as shown in FIGS. 8A and 9.

The therapy calibration submodule 604 functions similar to the assessment calibration submodule 502 and generates a therapy calibration GUI input form similar to the assessment calibration GUI input form 1250. In one aspect, the calibration GUI input form allows the user to communicate with and configure the pulse generation system 106 and the orofacial stimulator appliance 108 to verify the intended function and calibration of the instruments prior to the start of the therapy session.

Figure 29:
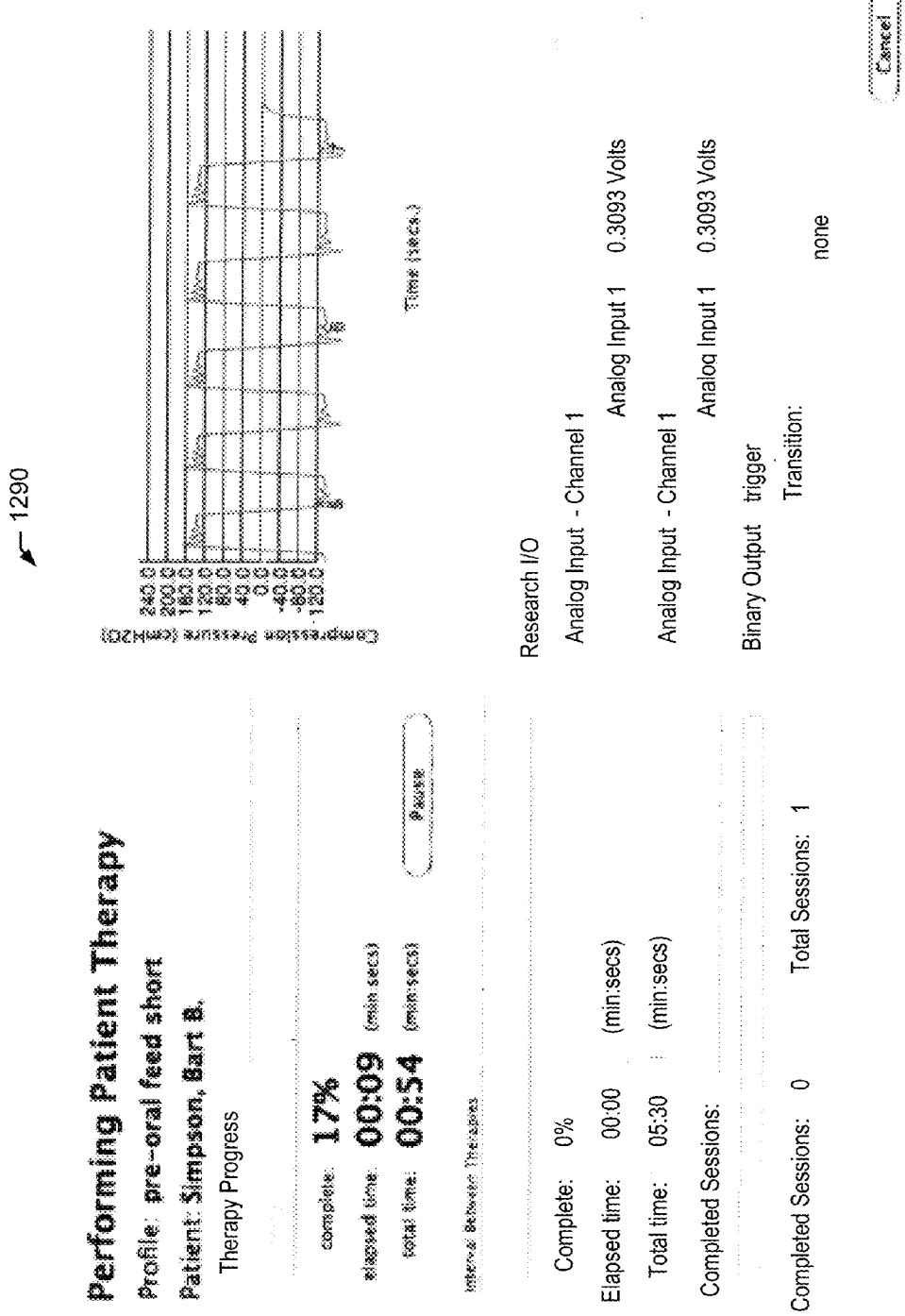

The therapy execution submodule 604 captures and displays the patient's NNS pattern activity during a therapy session. The therapy execution submodule 604 may generate a display 1290, as shown in FIG. 29, that shows progress of the therapy session at the start of the session, during the therapy session, at a rest interval, and at the conclusion of the therapy session, respectively. In other aspects, fewer or a greater number of displays may be provided during the therapy session.

Similar to an assessment session, the therapy session may be initiated by input received through the start control button 1278 of the GUI input form 1276. Alternately, the therapy session may be initiated by a switch 816 on a handpiece 806 of the orofacial stimulator appliance 108. The switch 816 may be any suitable switch including, but not limited to a push-button switch or a toggle switch. Further, the switch 816 may be used to alternate between a therapy mode and an assessment mode and/or to activate the therapy mode or assessment mode.

After a therapy session, the post-therapy review submodule 606 generates a post-session GUI input form similar to the assessment post session GUI input form 1274 where the user inputs notes regarding the therapy session. The user may indicate the state of alertness for the patient, such as alert, crying, drowsy, or sleepy.

The NNS application 204 further includes a leak detection module 306. The leak detection module 306 continuously monitors the performance of pneumatic subsystems within the pulse generator system 104 and the pneumatic lines and connections of the orofacial stimulator appliance 108 to detect air leaks.

Figure 30:
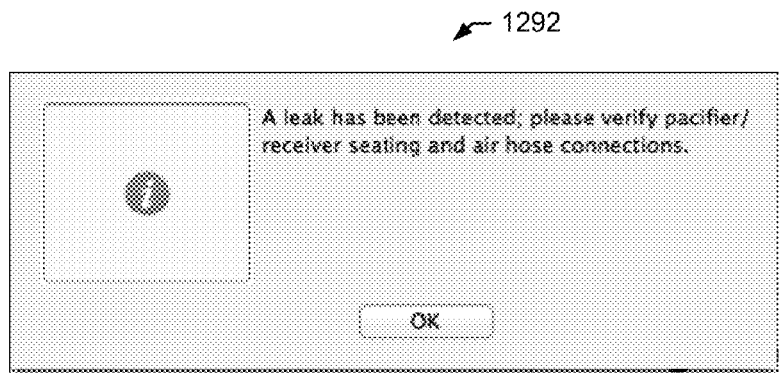

In one aspect, the leak detection module 306 determines that there may be an air leak by identifying reduced pulse amplitudes, increased pulse roll-offs, and/or the need for a greater stroke length in the pneumatic pulse generator 804 to generate the requested pressure. Further, the leak detection module 306 can identify air leaks caused by disconnected airlines, and poorly seated receiver tubes or pacifiers. The module 306 will display a warning 1292, as shown in FIG. 30, requiring the user to address the leak. The leak detection module 306 may monitor the therapeutic stimulus system 100 automatically and continuously during both assessment and therapy sessions.

The NNS application 204 also includes the research module 308 that allows a user of therapeutic stimulus system 100 to conduct various research experiments and protocols. In particular, the research module 308 receives and transmits data to an input/output (I/O) port of the computing device 102 or the real-time controller 800 of the pulse generation system 106. The I/O port, in turn, may be in communication with any of a variety of external instruments for conducting research.

In various other aspects, the NNS application 204 may include additional modules for other functions, including those typically associated with medical or rehabilitation facilities. By way of example and not limitation, the NNS application 204 may also include a billing module to interface with an existing billing system or a printing module for printing various data, charts, or reports.

The NNS Therapeutic Appliance Assembly

Referring now to FIGS. 1, 8A-B, and 9, the NNS Therapeutic appliance assembly includes the pulse generation system 106 and the orofacial stimulator appliance 108.

During an assessment session, the computing device 102 may record and display a signal received from a pressure transducer 808 of the orofacial stimulator appliance 108, as shown in FIG. 8B. The transducer 808 translates pressure changes caused by sucking and mouthing movements of the patient into an analog signal that tracks the pressure applied to a pacifier 810 versus time. The analog pressure signal is converted to a digital signal at an analog-to-digital convertor 802 of the pulse generation system 106, as shown in FIG. 8A. The analog-to-digital converter 802 is incorporated into a real-time controller 800, that receives and modifies received and/or generated pressure signals in real-time. The digital pressure signal is then received, recorded, and displayed by the assessment module 302.

Similarly, in one aspect of a therapy session, the pulse generation system 106 receives amplitude data 900 and pulse duration data 902 for the desired waveforms. The amplitude data 900 and the pulse duration data are provided to the real-time controller 800 which may include an H-bridge (not shown) and a proportional—integral—derivative controller (PID controller) 904. By way of example and not limitation, the PID controller 904 may be a CompactRIO controller. The PID controller 904 generates a signal 906 that is fed through a pulse-width modulation (PWM) component 908. The modulated signal 910 is then provided to a motor 912 of the pneumatic pulse generator 804. In one embodiment, the pneumatic pulse generator 804 consists of a linear motor 912 mechanically engaged to an air cylinder, such as but not limited to an Airpel® airpot or other device having a piston fitted in a precision bore cylinder with position and pressure feedback sensors in communication with the PID controller 904. The pulse generator 804 also includes a position feedback sensor 916 to monitor the position of the piston of the dashpot 914 and a pressure feedback sensor 918 to monitor the pressure with the dashpot 914. The air displaced by the pneumatic pulse generator 804 is then transmitted to the handpiece 806, through one or more pneumatic airlines, where the therapy waveform displaces the outer surface of the pacifier 810. The pulse generator 804 may also include a vent valve 920 that is normally closed, however the valve may be opened and vented to atmosphere to ensure pressure equilibrium at the start of each assessment or therapy session. Optionally, the pulse generator 804 may also include another valve (not shown) that isolates the dashpot 914 from the handpiece 806 during a Power-On Self Test (POST). The optional valve therefore permits diagnostic testing of the therapeutic stimulus system 100.

The orofacial stimulator appliance 108 includes the handpiece 806 and the pacifier 810 that are brought into contact with the patient to deliver the therapeutic stimuli. In one aspect, the handpiece 806 includes a receiver tube 812 in fluid communication with the interior of the baglet or pacifier 810. The receiver tube 812 includes an interior void for receiving a volume of air from the pneumatic pulse generator 804 or from the pacifier 810. Optionally, the handpiece 806 also includes a receiver tube insert 814, that may be inserted in to the receiver tube 812 to limit the total volume of air in the interior void of receiver tube. The handpiece 806 may also include a mode valve 922 that is opened or closed depending on whether an assessment session or a therapy session is to be performed.

In other aspects, the orofacial stimulator appliance 108 may include a piezoelectric system for generating an electrical charge in response to a mechanical stress or generating a mechanical stress in response to an electrical charge. Further, the orofacial stimulator appliance 108 may produce or at least project sound waves to deliver the therapeutic stimuli. For example, the orofacial stimulator appliance 108 may include a speaker or other electroacoustic transducer (not shown) to project sonic waves that stimulate the patient. The signals 906 and 910 or a signal to generate the sonic wave may be high-velocity signals. Preferably, the stimulus provided by the displacement of the outer surface of the pacifier 810 is recognized above and beyond any background activity or noise of the patient or the therapeutic stimulus system 100.

In one aspect, the expansion characteristics of the therapy pulses as delivered by expansion of the pacifier are verified using a laser micrometer (not shown). The data from the laser micrometer regarding the frequency and amplitude components of the therapy pulse at the pacifier 810 may be digitized, recorded, and analyzed by the NNS application 204.

Preferably, the pacifier 810 is a Soothie NICU® pacifier or a Wee Soothie® pacifier; however, the size, shape, and/or type of pacifier 810 may vary between procedures and/or patients. In addition, one or both of the pulse generation system 106 and the orofacial stimulator appliance 108 may be configured for each particular patient.

The Therapeutic Waveform

Figure 10A:
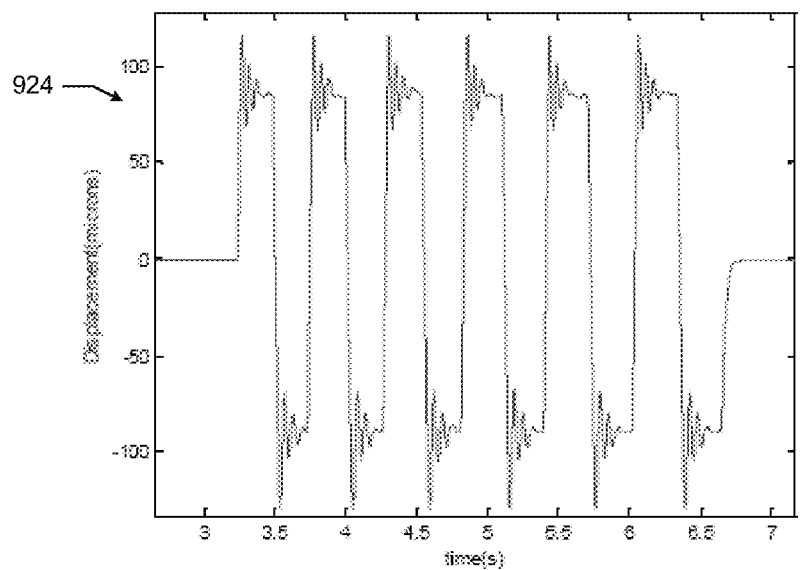
FIG. 10A is a graph depicting the displacement of pacifier in response to a therapeutic pressure pulse sequence according to one aspect.
Figure 10B:
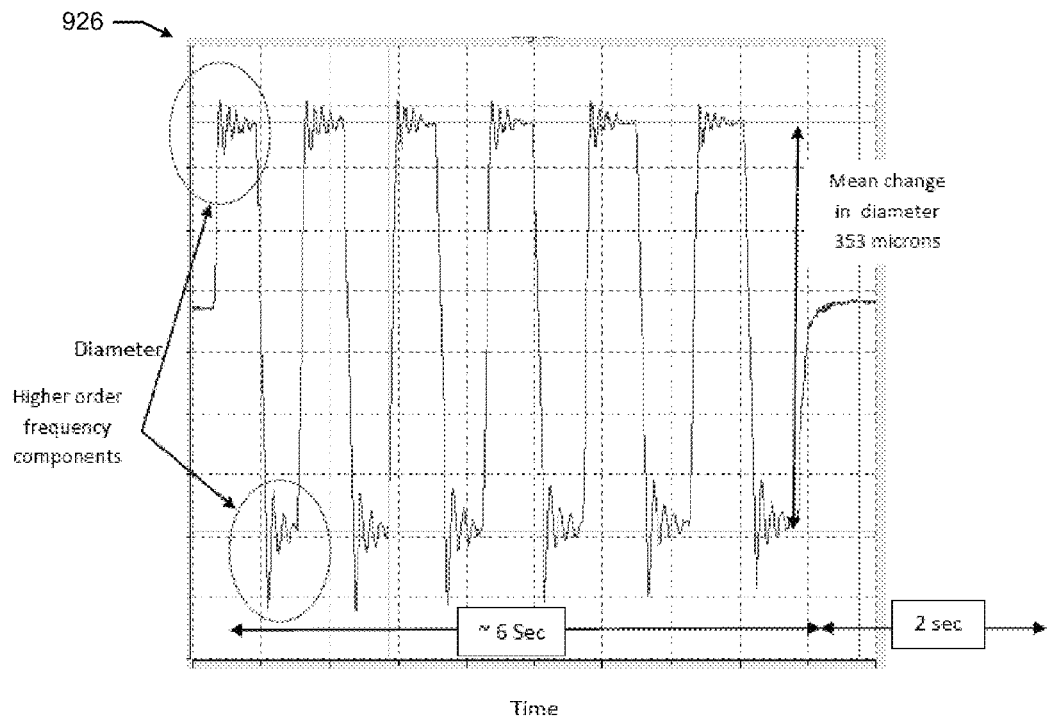
FIG. 10B is a graph depicting the change in the mean diameter of a pacifier in response to a pressure pulse according to one aspect.

Preferably, the therapy waveform consists of one or more salient therapeutic bursts and each burst contains two or more square wave pulses. Typically, the bursts are separated by a configurable and variable delay interval. FIGS. 10A and 10B depict plots 924 and 926 that indicate changes in the pacifier 810 in response to a sequence of the therapy waveforms.

According to one aspect, the nominal number of pulses in a desired therapeutic burst is six, while the actual number is configurable by users of the therapeutic stimulus system 100. Preferably, each pulse in a therapeutic burst is a square wave pulse having the same configurable amplitude. Further, the period of each pulse increases sequentially thereby, causing the waveform frequency to slow down from the start of the therapeutic burst to the end of the therapeutic burst. A desirable decelerating sequence pulse sequence has periods of approximately $510\pm3$ ms, $526\pm3$ ms, $551\pm3$ ms, $580\pm3$ ms, and $626\pm3$ ms between therapeutic bursts. When more than five pulses are used in the therapeutic burst, the sixth and all subsequent pulses have an periodic interval of approximately 626 ms.

Figure 10C:
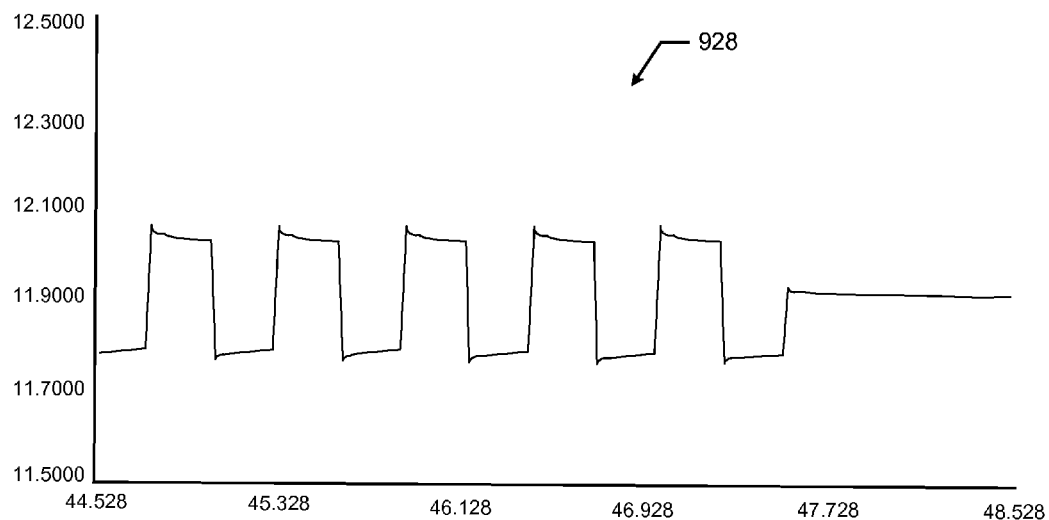
FIG. 10C is a graph depicting a therapeutic burst according to one aspect.
Figure 10D:
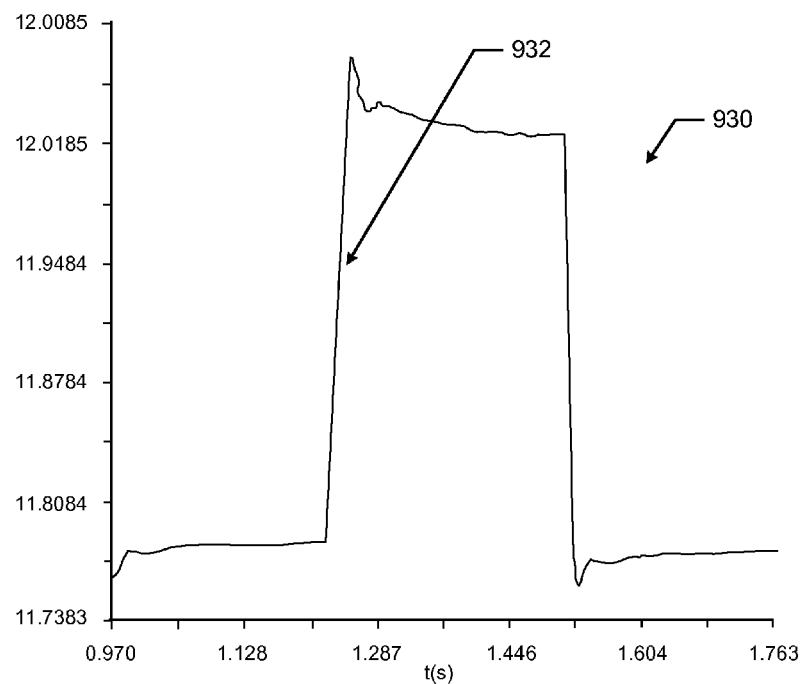
FIG. 10D is a graph depicting a square wave pulse according to one aspect.

Preferably, each square wave pulse period is shaped to minimize the positive and negative rise/fall times. For example, the transition intervals of each pulse's leading or trailing edges between each pulse may be tuned to create harmonics of $1.7\pm0.5$ Hz, $5.5\pm0.5$ Hz, $9.0\pm0.5$ Hz, $12.5\pm0.5$ Hz, and $16.5\pm0.5$ Hz. It is desired that the therapy waveform have minimal ringing or flutter at the square wave peaks, in order to be perceived as a "clean" square waves. As the therapy pulse profiles may be modified in the amplitude and frequency domains, a power spectrum analysis shows that the preferred therapy waveform generates displacement of the pacifier 810 at a fundamental frequency of approximately 1.7 Hz and higher orders. This fundamental frequency is preferred to entrain the patient's nervous system through cutaneous signal detection. Further, the preferred therapy waveform has a Q factor greater than or equal to $\frac{1}{2}$. As such, the relative high frequency of the rising and falling edges of the therapy pulse helps to achieve stimulus salience in the patient. During a therapy session, the surface of the pacifier 810 may experience one or more positive displacements, one or more negative displacements, or combinations thereof, including but not limited to alternating between positive and negative displacements. A therapeutic burst 928 having square wave pulses to cause only positive displacement of a pacifier surface is shown in FIG. 10C. Similarly, FIG. 10D depicts a single square wave pulse 930 having a rapid rise time, indicated generally as 934, of approximately 0.017 ms. The rapid rise times of the square wave pulse, which is typically less than about 190 ms and particularly those less than about 50 ms, are significantly more effective than low-velocity stimulus patterns having rise/fall times of approximately 190 ms or greater in providing patients with a beneficial and salient neurotherapy.

In all aspects, the number of square wave pulses per therapeutic burst, the number of therapeutic bursts per therapy session, and the amplitude of the square wave pulses are configurable by the user to account for variability in the patients. For example, the age, endurance, and/or aptitude of the patients may vary, thereby requiring the user to select or modify a therapy pulse profile via the therapy configuration submodule 600.

Figure 10E:
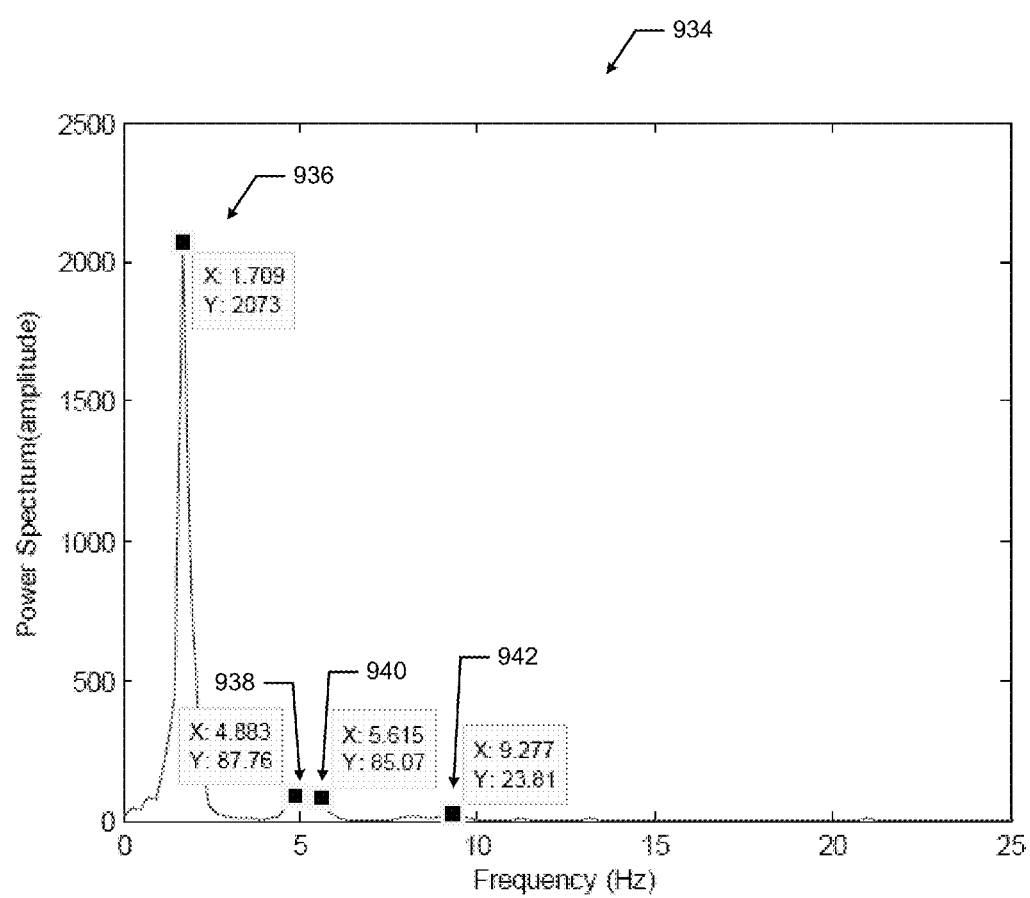
FIG. 10E is a graph depicting a power spectrum of a square wave pulse according to one aspect.

By way of example and not limitation, FIG. 10E depicts a power spectrum 934 of one exemplary square wave pulse. As shown, a fundamental frequency of approximately 1.709 Hz is generally indicated as 936. In contrast to lower velocity pulses, the square wave pulse includes several harmonics, generally indicated as 938-942, that transfer energy at approximately 4.883, 5.615, and 9.277 Hz, respectively. The additional high frequency components 938-942 present in the square wave pulse contribute significantly to its tactile signature as a higher velocity signal.

FIGS. 10F-I illustrate the adjusted means and standard errors resulting from a multivariate statistical analysis that compared the effectiveness of the high-velocity pulse (HVP) versus a low-velocity pulse (LVP) as they relate to four orofacial behaviors. FIGS. 10F-I depict the combined adjusted means for a control group, a group exposed to LVPs (LVP group), and a grouped exposed to HVPs (HVP group). Each of the groups used in the analysis were composed of four clinical sub-groups of preterm infants, including healthy infants, infants having respiratory distress syndrome, infants having chronic lung disease, and infants with diabetic mothers.

Figure 10F:
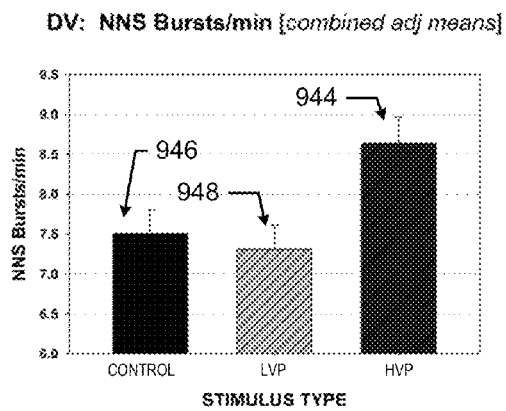
FIGS. 10F-I depict the results of analysis comparing the effects of various pulses as they relate to orofacial behaviors.
Figure 10G:
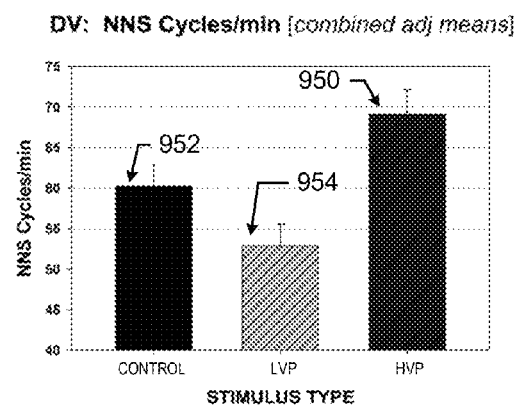
Figure 10H:
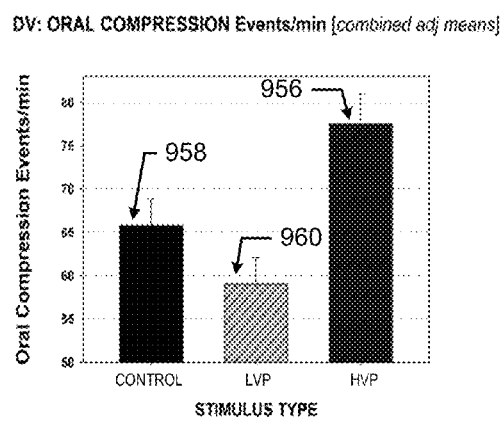
Figure 10I:
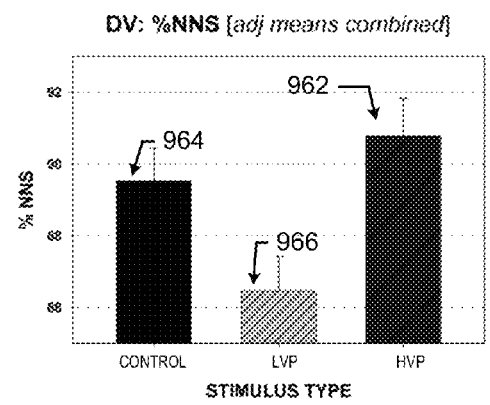

In particular, FIG. 10F, illustrates that the HVP group, as indicated by 944, generated a greater number of NNS Bursts per minute than the control group, as indicated by 946, and the LVP group, as indicated by 948. Similarly, FIG. 10G illustrates that the HVP group, as indicated by 950, generated a greater number of NNS Cycles per minute than the control group, as indicated by 952, or the LVP group, as indicated by 954. FIG. 10H illustrates that the HVP group, as indicated by 956, generated a greater number of oral compression events per minute than the control group, as indicated by 958, or the LVP group, as indicated by 960. Likewise, FIG. 10I illustrates that the HVP group, as indicated by 962, generated a higher absolute percentage of NNS events relative to the total oral compressions per minute than the control group, as indicated by 964, or the LVP group, as indicated by 966. As shown, the HVP group exceeded the control group and the LVP group, thus indicating that the HVP is providing a greater neurotherapeutic benefit to the collective group of preterm infants. Further, within each HVP group, the infants having respiratory distress syndrome, infants having chronic lung disease, and infants with diabetic mothers benefited more from the HVP stimulus than did the healthy infants.

Methods of Using the Non-nutritive Suck Entrainment System (Entrainment System)

Figure 11A:
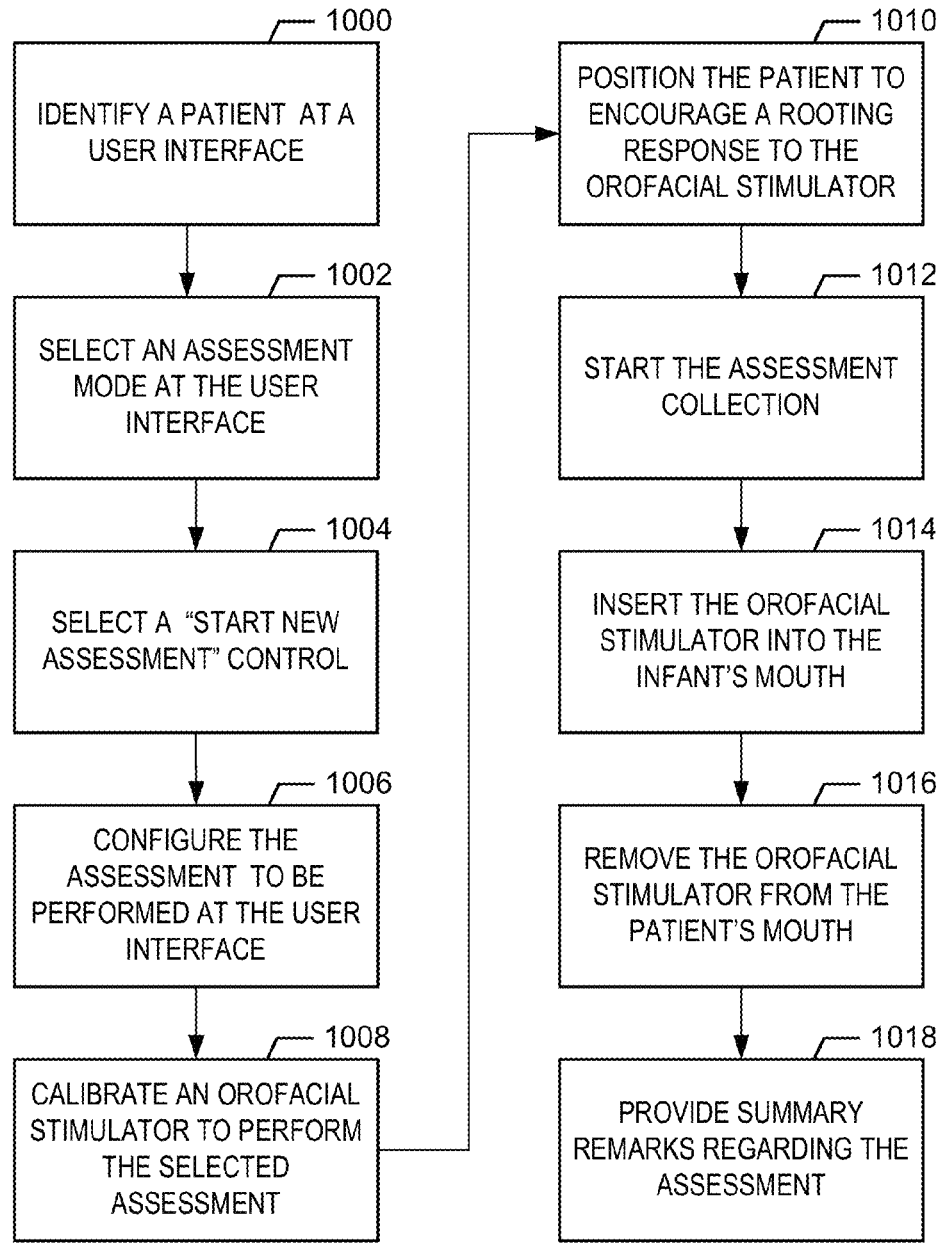
FIG. 11A illustrates a method for assessing a non-nutritive suck pattern according to one aspect of the therapeutic stimulus system.

FIG. 11A illustrates a method for performing an assessment session to capture and analyze a patient's NNS pattern in accordance with an aspect of the therapeutic stimulus system 100. At step 1000, a user of the therapeutic stimulus system 100 selects a patient from a displayed list of patients. The user then selects a control button to enter the assessment mode of the NNS application 204 at step 1002 and selects the "start new assessment" control button 1224 at step 1004. The assessment session is configured as desired at step 1006 based upon the patient's age, injury, or other patient data 702 and optionally, data 704 regarding the patient's assessment history. The orofacial stimulator appliance 108 is calibrated at step 1008, while the patient is positioned to encourage a rooting response to the orofacial stimulator appliance at step 1010. At step 1012, the assessment session is started, while the orofacial stimulator appliance is contacted with the patient's lips and mouth at step 1014. In other aspects, the orofacial stimulator appliance 108 is inserted into the patient's mouth at step 1014. Similarly, in other aspects, the steps 1012 and 1014 may be reversed.

Once the assessment session is completed, the orofacial stimulator appliance 108 is removed from the patient at step 1016. After the feature extraction submodule 406 analyzes the collected assessment data, using the input form 1274 generated by the post-assessment review module 508. After the assessment session, the user may initiate another assessment session for the same patient or a different patient. Alternatively, the user may instead exit the NNS application 204.

Figure 11B:
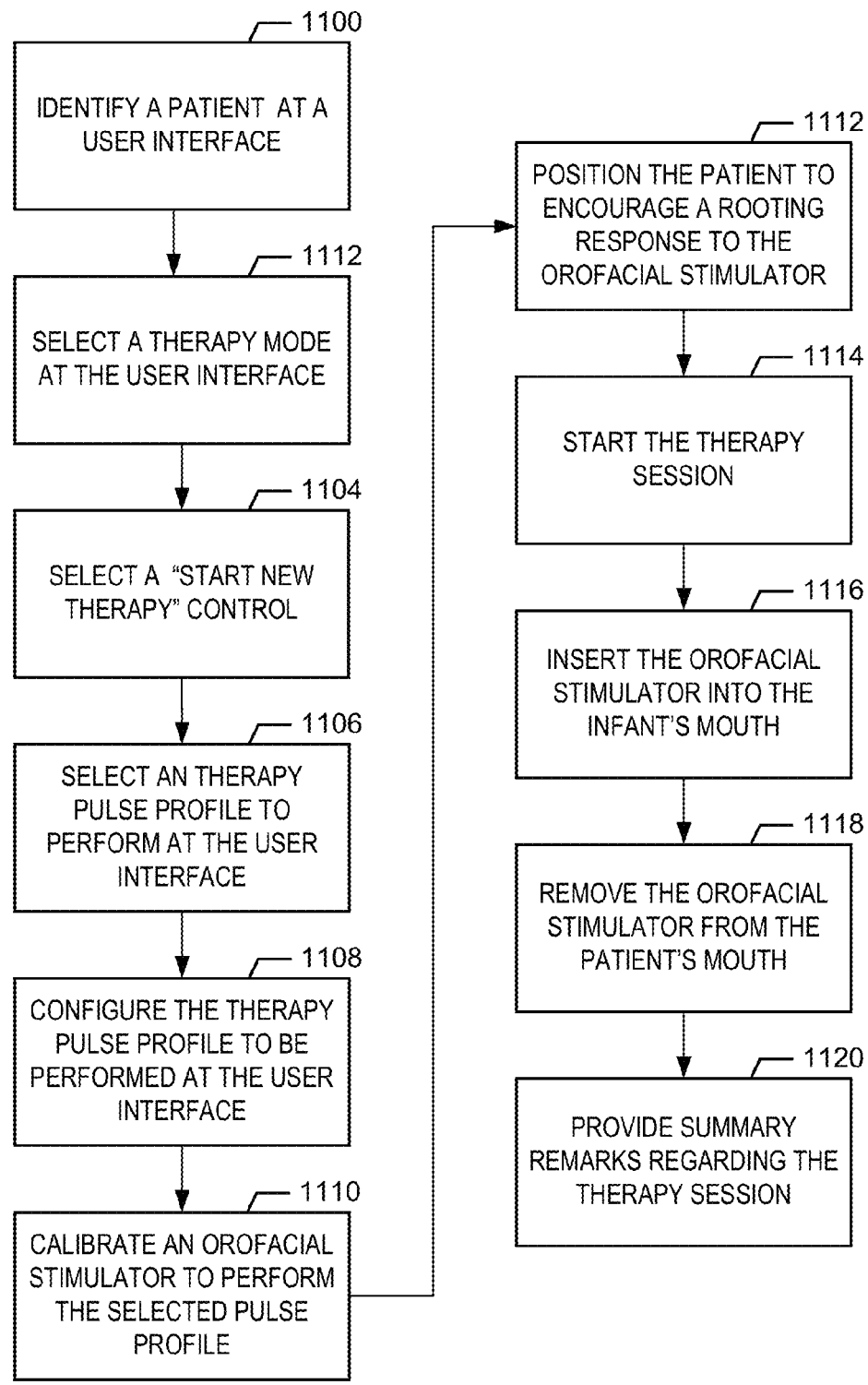
FIG. 11B illustrates a method for stimulating a patient to entrain an organized non-nutritive suck pattern according to one aspect of the therapeutic stimulus system.

FIG. 11B illustrates a method for performing a therapy session to entrain a patient's sCPG to generate an organized NNS pattern in accordance with an aspect of the therapeutic stimulus system 100. At step 1110, a user of the therapeutic stimulus system 100 selects a patient from a list of patients. The user then selects a control button to enter the therapy mode of the NNS application 204 at step 1102 and the selects a "start new therapy" control button 1278 at step 1104. The therapy pulse profile to be generated during the therapy session is selected from the therapy pulse profile data 708 at step 1106 and at step 1108, the therapy pulse profile is configured as desired based upon the patient's age, injury, or other patient data 702 and any of the patients NNS assessment data 704. The orofacial stimulator appliance 108 is calibrated at step 1110, while the patient is positioned to encourage a rooting response to the orofacial stimulator appliance at step 1112. At step 1114, the therapy session is started, while the orofacial stimulator appliance is contacted with the patient's lips and mouth at step 1116. In other aspects, the orofacial stimulator appliance 108 is inserted into the patient's mouth at step 1116. Similarly, in other aspects, the steps 1114 and 1116 may be reversed. During the therapy session, the user may attempt to hold the patient as still as possible.

Once the therapy session is completed, the orofacial stimulator appliance 108 is removed from the patient at step 1118. The user may provide summary remarks regarding the therapy session at step 1120 using the GUI input form 1274 generated by the post-therapy review module 606. After the therapy session, the user may initiate another therapy session for the same patient or a different patient. Alternatively, the user may instead exit the NNS application 204.

Exemplary Methods of Use by a Medical Professional to Treat an Individual with Impaired Neural Function An exemplary method of using the therapeutic stimulus system 100 by a medical professional to treat a patient having impaired neural function includes an initial step of powering on the various components of the NNS system, including the pulse generation system 106 and the computing device 102. Optionally, the user may verify that a back-up power supply, such as a battery, is properly connected, such that the use of the NNS system will not be compromised by a loss of power.

After accessing the computing device and executing the NNS application 204, the user logs in to the NNS application, by selecting their username from a displayed list of approved usernames. The user then inputs their password to log in to the NNS application. The medical professional may now access the records of an existing patient to perform an assessment or provide therapeutic stimulation. Alternately, the user may enter and save data regarding a new patient to the NNS system.

To begin an assessment session, the user selects the patient's name in a displayed "Active Patient List". Next, the user selects "Assessment" to enter the assessment mode of the NNS application. The user then selects a "Start New Assessment" control button and enters data into a displayed "Configuring Assessment" user interface. The user may enter, for example, the estimated minutes required for assessment and the color or type of pacifier to be used. After entering the data, the user continues and may select a displayed "Calibrate" control button, or depress the switch on the handpiece to automatically calibrate the system.

The user moves and positions the therapeutic stimulus system near the patient and encourages the patient to take the pacifier into their mouth. To begin the assessment session, the user presses the hand-piece button or selects a displayed "Start" control button, and gently places the pacifier in the infant's mouth. During the session, the user may press the hand-piece button or a displayed "Pause/Resume" control button to pause the session. The assessment session will automatically stop when the designated time is complete, and the user may then gently remove the pacifier from infant's mouth. To complete the assessment session, the user touches a "Close" control button, enters additional data in the displayed "Session summary" display, and finally concludes the session by selecting a "Done" control button.

To begin therapy session, the user powers on the system and executes the NNS application, similar to the steps of performing an assessment session. The user selects the patient's name in the displayed "Active Patient List". Next, the user selects "Therapy" to enter the therapy mode of the NNS application. The user then selects a "Start New Therapy" control button and enters data into a displayed "Configuring Therapy" user interface. The user may select the type of therapy most appropriate for the patient. For example, the user may select a "Pre Oral Feed" control button to perform for a three minute therapeutic session prior to a patient's oral feeding. Conversely, the user may select "Gavage Feed" control button to provide therapeutic stimulus in combination with a non-oral feeding. After selecting the therapy type, the user continues and may select a displayed "Calibrate" control button, or depress the switch on the handpiece to automatically calibrate the system.

The user moves and positions the therapeutic stimulus system near the patient and encourages the patient to take the pacifier into their mouth. To begin the therapy session, the user presses the hand-piece button or selects a displayed "Start" control button, and gently places the pacifier in the infant's mouth. The user is reminded to hold the handpiece as still as possible during the therapy session. The therapy session will automatically stop when the designated time or therapy protocol is complete, and the user may then gently remove the pacifier from infant's mouth. To complete the assessment session, the user touches a "Close" control button, enters additional data in the displayed "Session summary" display, and finally concludes the session by selecting a "Done" control button.

Exemplary Methods of Use by a Medical Professional to Treat an Infant

An exemplary method of using the therapeutic stimulus system 100 by a medical professional to treat an infant having a deficient NNS pattern includes an initial step of powering on the various components of the NNS system, including the pulse generation system 106 and the computing device 102. Optionally, the user may verify that a back-up power supply, such as a battery, is properly connected, such that the use of the NNS system will not be compromised by a loss of power.

After accessing the computing device and executing the NNS application 204, the user logs in to the NNS application, by selecting their username from a displayed list of approved usernames. The user then inputs their password to log in to the NNS application. The medical professional may now access the records of an existing patient to perform an assessment or provide therapeutic stimulation. Alternately, the user may enter and save data regarding a new patient to the NNS system.

To begin an assessment session, the user selects the patient's name in a displayed "Active Patient List". Next, the user selects "Assessment" to enter the assessment mode of the NNS application. The user then selects a "Start New Assessment" control button and enters data into a displayed "Configuring Assessment" user interface. The user may enter, for example, the estimated minutes required for assessment and the color or type of pacifier to be used. After entering the data, the user continues and may select a displayed "Calibrate" control button, or depress the switch on the handpiece to automatically calibrate the system.

The user positions the swaddled infant in a relaxed position or a feeding position and encourages a rooting response to pacifier. To being the assessment session, the user presses the hand-piece button or selects a displayed "Start" control button, and gently places the pacifier in the infant's mouth. During the session, the user may press the hand-piece button or a displayed "Pause/Resume" control button to pause the session. The assessment session will automatically stop when the designated time is complete, and the user may then gently remove the pacifier from infant's mouth. To complete the assessment session, the user touches a "Close" control button, enters additional data in the displayed "Session summary" display, and finally concludes the session by selecting a "Done" control button.

To begin therapy session, the user powers on the system and executes the NNS application, similar to the steps of performing an assessment session. The user selects the patient's name in the displayed "Active Patient List". Next, the user selects "Therapy" to enter the therapy mode of the NNS application. The user then selects a "Start New Therapy" control button and enters data into a displayed "Configuring Therapy" user interface. The user may select the type of therapy most appropriate for the patient. For example, the user may select a "Pre Oral Feed" control button to perform for a three minute therapeutic session prior to a patient's oral feeding. Conversely, the user may select "Gavage Feed" control button to provide therapeutic stimulus in combination with a non-oral feeding. After selecting the therapy type, the user continues and may select a displayed "Calibrate" control button, or depress the switch on the handpiece to automatically calibrate the system.

The user positions the swaddled infant in a relaxed position or a feeding position, as necessary, and encourages a rooting response to pacifier. To being the therapy session, the user presses the hand-piece button or selects a displayed "Start" control button, and gently places the pacifier in the infant's mouth. The user is reminded to hold the handpiece as still as possible during the therapy session. The therapy session will automatically stop when the designated time or therapy protocol is complete, and the user may then gently remove the pacifier from infant's mouth. To complete the assessment session, the user touches a "Close" control button, enters additional data in the displayed "Session summary" display, and finally concludes the session by selecting a "Done" control button.

The method may also be performed on patient's other infants. The method is substantially the same; however the patient is clothed and positioned as appropriate for the patient's age, physical condition, or any other factor deemed relevant to the patient's care.

It will be appreciated that the device and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore indicated by the appended claims rather than by the foregoing description. All changes, which come within the meaning and range of equivalency of the claims, are to be embraced within their scope.

What is claimed is:

1. A method for stimulating a suck central pattern generator and a trigeminal nerve in a brain of a human subject, such stimulation influencing brain response or brain development including repair of the brain, control of respiration, control of a non-nutritive suck pattern, mastication, and combinations thereof, the method comprising:
    contacting the human subject with an appliance to stimulate one or more nerve ending near the subject's mouth, including the facial region proximal to at least one lip and a tongue; and,
    actuating the appliance in response to a signal to generate a mechanical transfer of energy in at least one burst as an impulse sufficient to be recognized as a tactile stimulus by the subject's suck central pattern generator;
    wherein each burst comprises at least two square wave pulses of the same amplitude with the pulse period increasing with each successive pulse to form a decelerating pulse train sequence; and,
    wherein the square wave pulses range in frequency between 1.5 Hz and 5 Hz.

2. The method of claim 1, wherein at least six bursts in succession are contacted with the subject for at least two minutes at least twice a day.

3. The method of claim 1 wherein the square wave pulse displaces a surface of the appliance between about 150 microns and 300 microns for between 20 milliseconds and 50 milliseconds.

4. The method of claim 3, wherein the surface is displaced between about 260 microns and 300 microns.

5. The method of claim 3, wherein at least six bursts in succession are contacted with the subject for at least two minutes at least twice a day.

6. The method of claim 1 further comprising:
    stimulating an olfactory or auditory region.

7. The method of claim 1 wherein the appliance comprises a textured nipple, a pneumatic pulse generator, and a baglet, and wherein the appliance is in communication with a software system.

8. The method of claim 1 wherein the appliance comprises a piezoelectric system.

9. The method of claim 1 wherein the appliance projects sound waves to generate the square wave pulses.

10. The method of claim 1, wherein the tactile stimulus is above background activity of the subject and the signal is a high velocity signal.

11. The method of claim 1 wherein the subject is an infant with a congenital heart defect, wherein the congenital heart defect prevents the infant from feeding efficiently.

12. The method of claim 1 wherein the subject is a stroke patient, wherein the patient is unable to receive nourishment efficiently.

13. A system for stimulating a central pattern generator and a trigeminal nerve in a brain of a human subject, such stimulation influencing brain response or brain development including repair of the brain, control of respiration, control of a non-nutritive suck pattern, mastication, and combinations thereof, the system comprising:
    an orofacial stimulator appliance that, when actuated in response to a signal, generates a mechanical transfer of energy in at least one burst as an impulse sufficient to be recognized as a tactile stimulus by the subject's central pattern generator;
    wherein each burst comprises at least two square wave pulses of the same amplitude with the pulse period increasing with each successive pulse to form a decelerating pulse train sequence; and,
    wherein the square wave pulses range in frequency between 1.5 Hz and 5 Hz and are contacted with the subject for at least two minutes each day, at least twice a day for a minimum of five successive days.

14. The system of claim 13, wherein the orofacial stimulator appliance is in communication with a control application executable at a processor.

15. The system of claim 13, further comprising a pneumatic pulse generator that includes a PID controller and a pneumatic pulse generator, wherein the PID controller is an analog or real-time controller.

16. The system of claim 15, wherein the PID controller is a CompactRIO controller.

17. The system of claim 13, wherein each of the two or more square wave pulses comprises a harmonic of a base frequency.

18. The system of claim 13, wherein the harmonic for the two or more square wave pulses vary in frequency.

19. The system of claim 13, wherein the harmonic for the two or more pressure pulses are identical in frequency.

20. The system of claim 13, wherein each of the two or more pressure pulses have a damped harmonic profile.

21. The system of claim 20, wherein the damped harmonic oscillator profile of the two or more pressure pulses has a Q factor greater than or equal to ½.

22. The system of claim 13, wherein the signal further comprises a rest period yielding no displacement to the orofacial stimulator appliance.

23. The system of claim 13, wherein the processing device further comprises:
    a display device; and,
    an input device.

24. The system of claim 13, wherein the orofacial stimulator appliance further comprises:
    a handpiece;

a receiver tube;

a receiver tube insert; and, a pacifier.

25. The system of claim 24, wherein the handpiece comprises a push-button switch in communication with a control application.

26. A method for stimulating a central pattern generator and a trigeminal nerve in an adult human brain of an adult subject, such stimulation influencing brain response or brain development including repair of the brain, control of respiration, control of a non-nutritive suck pattern, mastication, and combinations thereof, the method comprising:

contacting the adult subject with an appliance to stimulate one or more nerve ending near the subject's mouth, including the facial region proximal to at least one lip and a tongue; and, actuating the appliance in response to a signal to generate a mechanical transfer of energy in at least one burst as an impulse sufficient to be recognized as a tactile stimulus by the subject's central pattern generator;

wherein each burst comprises at least two square wave pulses of the same amplitude with the pulse period increasing with each successive pulse to form a decelerating pulse train sequence; and, wherein the square wave pulses range in frequency between 1.5 Hz and 5 Hz.

27. The method of claim 26 wherein the burst displaces a surface of the appliance between about 260 microns and 300 microns for between 20 milliseconds and 50 milliseconds, and wherein at least six bursts in succession are contacted with the adult subject for at least two minutes, at least twice a day.

28. The method of claim 26 wherein a motion induced by the burst has an amplitude ranging between 260 microns and 300 microns.

29. The method of claim 26 wherein the pulses in the burst decelerate.

30. The method of claim 26 wherein the adult is contacted with a burst that comprises six pulses.

31. The method of claim 29 wherein the decelerating pulse train has period intervals of 510, 526, 551, 580, and 626 ms.

32. The method of claim 28 wherein the pulses have frequencies of 1.7 Hz, 5.5 Hz, 9.0 Hz, 12.5 Hz, and 16.5 Hz.

33. A method of using a square wave to stimulate the central pattern generator nerve, the method comprising:

contacting a human subject with an appliance to stimulate one or more nerve ending near the subject's mouth, including the facial region proximal to at least one lip and a tongue; and, actuating the appliance in response to a signal to generate a mechanical transfer of energy in at least one burst as an impulse sufficient to be recognized as a tactile stimulus by the subject's central pattern generator;

wherein each burst comprises at least two square wave pulses of the same amplitude with the pulse period increasing with each successive pulse to form a decelerating pulse train sequence;

wherein the square wave pulses range in frequency between 1.5 Hz and 5 Hz; and, wherein at least six bursts in succession are contacted with the subject for at least two minutes, at least twice a day.

\* \* \* \* \*